(12) United States Patent
Peumans et al.

(10) Patent No.: US 9,816,935 B2
(45) Date of Patent: Nov. 14, 2017

(54) INTEGRATED WAVEGUIDE STRUCTURE FOR FLUORESCENCE ANALYSIS

(71) Applicant: IMEC VZW, Leuven (BE)

(72) Inventors: Peter Peumans, Herfelingen (BE); Pol Van Dorpe, Spalbeek (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/113,122

(22) PCT Filed: Jan. 23, 2015

(86) PCT No.: PCT/EP2015/051421
§ 371 (c)(1),
(2) Date: Jul. 21, 2016

(87) PCT Pub. No.: WO2015/110614
PCT Pub. Date: Jul. 30, 2015

(65) Prior Publication Data
US 2017/0003227 A1    Jan. 5, 2017

(30) Foreign Application Priority Data
Jan. 23, 2014    (EP) .................................. 14152222

(51) Int. Cl.
*G02B 6/12* (2006.01)
*G01N 21/77* (2006.01)
(Continued)

(52) U.S. Cl.
CPC ....... *G01N 21/7746* (2013.01); *G01N 21/648* (2013.01); *G01N 21/6428* (2013.01);
(Continued)

(58) Field of Classification Search
None
See application file for complete search history.

(56) References Cited

U.S. PATENT DOCUMENTS

| 7,384,797 | B1 * | 6/2008 | Blair | .................. G01N 21/6452 |
| | | | | 385/12 |
| 7,951,583 | B2 * | 5/2011 | Duer | .................... G01N 21/253 |
| | | | | 385/12 |

(Continued)

OTHER PUBLICATIONS

PCT International Search Report and Written Opinion, PCT International Application No. PCT/EP2015/051421, dated Apr. 10, 2015, 12 pages.
Sanchis, Pablo et al., "Highly Efficient Crossing Structures for Silicon-On-Insulator Waveguides", Optics Letters, vol. 34, No. 18, Sep. 15, 2009, pp. 2760-2762.

(Continued)

*Primary Examiner* — Sung Pak
(74) *Attorney, Agent, or Firm* — McDonnell Boehnen Hulbert & Berghoff LLP

(57) ABSTRACT

The present disclosure relates to structures, systems, and methods for characterizing one or more fluorescent particles. At least one embodiment relates to an integrated waveguide structure. The integrated waveguide structure includes a substrate. The integrated waveguide structure also includes a waveguide layer arranged on top of the substrate. The waveguide layer includes one or more excitation waveguides, one or more emission waveguides, and a particle radiation coupler, which includes a resonator element. In addition, the integrated waveguide structure includes one or more sensing sites configured with respect to the one or more excitation waveguides and the one or more emission waveguides such that a fluorescent particle at one of the sensing sites is activated by an excitation radiation transmitted via the one or more excitation waveguides and radiation emitted by the fluorescent particle is coupled into at least one of the emission waveguides by the particle radiation coupler.

20 Claims, 16 Drawing Sheets

(51) Int. Cl.
*G01N 21/64* (2006.01)
*G02B 6/125* (2006.01)
*G02B 6/122* (2006.01)

(52) U.S. Cl.
CPC ......... *G01N 21/6452* (2013.01); *G02B 6/125* (2013.01); *G01N 2021/6439* (2013.01); *G01N 2021/7716* (2013.01); *G01N 2021/7786* (2013.01); *G02B 6/1228* (2013.01)

(56) References Cited

U.S. PATENT DOCUMENTS

| | | | |
|---|---|---|---|
| 9,423,397 B2* | 8/2016 | Duer | G02B 6/4226 |
| 2005/0077513 A1* | 4/2005 | Fan | G01N 21/552 |
| | | | 257/45 |
| 2006/0008227 A1* | 1/2006 | Schmidt | G01N 21/0303 |
| | | | 385/129 |
| 2006/0197960 A1* | 9/2006 | Bazylenko | G01N 21/253 |
| | | | 356/491 |
| 2009/0312188 A1* | 12/2009 | Duer | B01L 3/502715 |
| | | | 506/6 |
| 2010/0092341 A1* | 4/2010 | Hummel | G01N 21/648 |
| | | | 422/82.08 |

OTHER PUBLICATIONS

Krioukov, E. et al., "Performance of Integrated Optical Microcavities for Refractive Index and Fluorescence Sensing", Sensors and Actuators, vol. 90, 2003, pp. 58-67.

\* cited by examiner

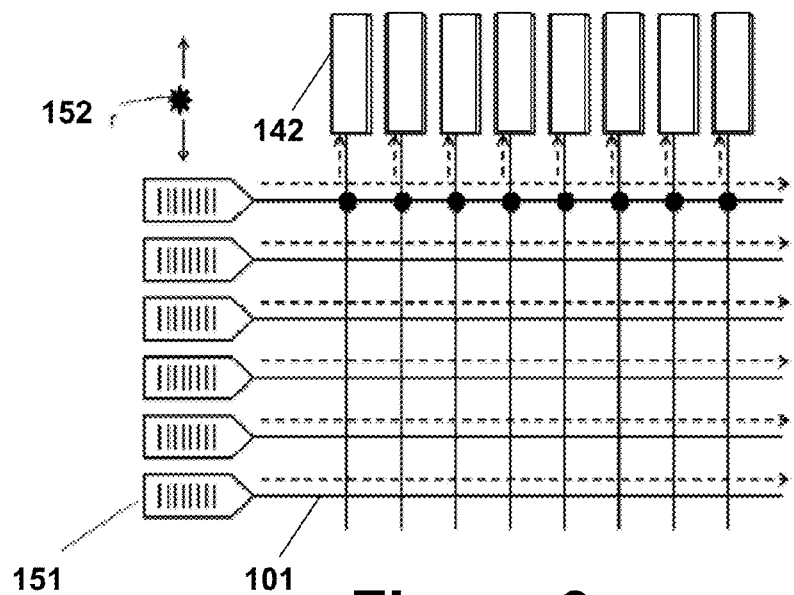
Figure 9
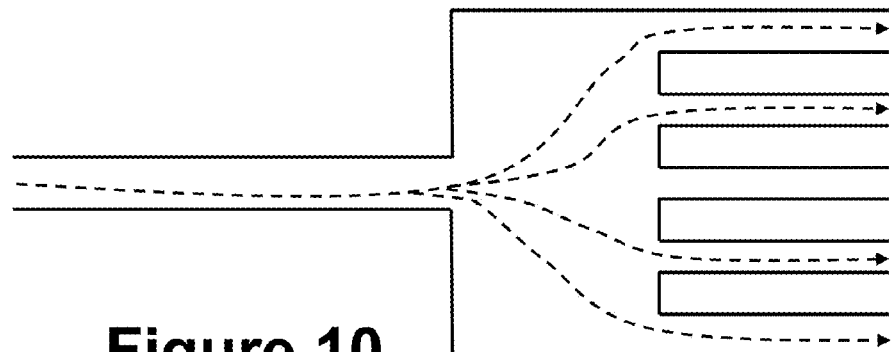
Figure 10
| 200 | |
|---|---|
| 201 | coupling light into an excitation waveguide |
| 202 | activating label of bioparticle |
| 203 | coupling emitted light to an emission waveguide via resonator |
| 204 | detecting emitted light |
Figure 11

Z=0 nm

Z=188 nm

Z=375 nm

Z=563 nm

Z=750 nm

Z=938 nm

Z=0 nm

Z=188 nm

Z=375 nm

Z=563 nm

Z=750 nm

Z=938 nm

INTEGRATED WAVEGUIDE STRUCTURE FOR FLUORESCENCE ANALYSIS

CROSS-REFERENCE TO RELATED APPLICATION

The present application is a national stage entry of PCT/EP15/051421 filed Jan. 23, 2015, which claims priority to European Patent Application No. 14152222.7 filed on Jan. 23, 2014, the contents of each of which are hereby incorporated by reference.

FIELD OF THE INVENTION

The invention relates to the field of fluorescence analysis. More specifically it relates to integrated photonic systems for studying biological samples, such as proteins or DNA sequences including single particle fluorescence analysis.

BACKGROUND OF THE INVENTION

Single-molecule fluorescence (SMF) enables the detailed study of biological processes with unprecedented resolution. Therefore, SMF has become an important tool for unravelling the biological machinery in cells. SMF has for example been used in examining cellular signal transduction pathways, protein-protein interactions and protein folding. Unfortunately, progress in current SMF technologies may have been hampered by the complex optical set-ups needed to perform such experiments.

Generally, in SMF applications, one wants to probe the fluorescence of single molecules in a large background of other fluorescent molecules, e.g. for studying protein or DNA structure and/or dynamics. This is problematic, as all fluorescent molecules in the illuminated area are probed simultaneously. Since the spot size of a focused laser beam is limited by the diffraction limit, the concentration of fluorescent molecules has to be reduced. Some SMF imaging concepts known in the art may effectively dilute the concentration by randomly switching on and off the molecular fluorescence. However, this is less trivial for probing molecular dynamics, which can be tackled by tightly focusing laser beams in confocal microscopes to reduce the excitation volume and by simultaneously reducing the concentration of fluorescent molecules such that at any time only a few molecules are excited and probed.

Fluorescence is also widely used for sensing of small concentrations of biomolecules in samples, e.g. in body fluids, in order to determine the concentration of certain biomarkers. These sensing principles generally rely on assays with several washing steps to remove dye molecules that have not reacted with analyte molecules. Here as well, a highly confined excitation region provides the possibility to perform wash-free sensing assays, where the binding of the fluorescent molecules on the surface of the substrate can be monitored without the need to wash away the solution after the binding. A wash-free assay allows to measure biomolecular interactions in real-time and greatly simplifies the overall assay protocol and the sample/liquid handling system that is needed. The latter may especially be beneficial for highly integrated, handheld devices.

In the recent past, nanophotonic techniques have been established to reduce the excitation volume. For example, In molecular fluorescence analysis, e.g. of DNA sequences, it is known in the art to immerse a substrate comprising a plurality of pores, e.g. nano-pores, in a liquid comprising the biological sample to analyze and one or more chemically reactive derivatives of at least one fluorophore. For example, the liquid may comprise single stranded DNA and a mixture of the 4 DNA nucleotides, A, C, G and T, each nucleotide labeled with a specific fluorescent tag for emitting a specific colour upon optical excitation. In the pores a processing enzyme, e.g. DNA polymerase, may be immobilized for promoting a chemical reaction between the biological sample to analyze and the chemically reactive fluorophore derivative(s). For example, DNA polymerase in the pore may progressively convert single stranded DNA into double-stranded DNA by adding the complimentary nucleotides one by one. When the biological sample and the chemically reactive fluorophore derivative(s) react under influence of the processing enzyme, e.g. when a nucleotide is incorporated in the DNA strand, it is optically excited by a radiation source that illuminates each pore. After excitation, the fluorescent tag emits radiation of a specific wavelength. A lens may be used to focus the emitted radiation, which may then be recorded by an image sensor. To avoid distortion of the emitted radiation signal, an excitation rejection filter can be used to block excitation radiation from reaching the image sensor, e.g. such that only the emitted radiation reaches the detector. A colour separation element may furthermore be used to spectrally disperse the emitted radiation on different parts of the detector, or on different detectors.

It is furthermore known in the art to surround the pores with a suitable metal, such that the pores may be considered to be zero mode waveguides. The zero mode waveguide (ZMW), e.g. a sub-wavelength aperture in a metal film, can advantageously reduce the excitation volume to the nanometer range. The ZMW approach may for example be particularly suitable for single molecule real-time DNA sequencing.

However, the optics, e.g. lenses, which are used for illumination and collection of the emitted radiation in such prior-art systems can be expensive and bulky. Particularly, expensive microscope setups and high numerical aperture (NA) optics may be required. Furthermore, the colour separation filter needed for dispersing the emitted radiation on different parts of the detector add to the complexity and cost of such system. Another disadvantage of such systems may be that the throughput speed can be rather limited, e.g. the number of pores is limited due to the area constraints imposed by the optics, and a cost-effective parallelization of the technique is hampered by the high cost of the optical components.

While progress has been made on SMF using free-space optics, several bulky optical components and their circuits can also be integrated on chip. The technology of nano-photonics, which is based on high index contrast waveguides, has progressed tremendously and especially optical waveguide circuits based on silicon are becoming a mature technology platform. For example, waveguides constructed from silicon in a $SiO_2$ cladding have shown great potential at telecom wavelengths, although silicon is a strong absorber in the visible wavelength region and therefore not a good material for guiding visible radiation. Molecular fluorescence, however, usually takes place at visible wavelengths, as in this range a lot of high brightness fluorescent dyes are available that can be efficiently coupled to a wide range of biomolecules and cells. In the visible spectrum, alternatives to silicon are, for example, SiN, GaP or $TiO_2$ based waveguides.

For example, the publication "Performance of integrated optical microcavities for refractive index and fluorescence sensing" by Krioukov et al., in Sensors and Actuators B 90, pp. 58-67, a fluorescence sensor is disclosed which comprises integrated waveguides and an integrated optical disk microcavity. Such sensor may obtain a good sensitivity for detecting fluorescence emissions of an analyte. According to this prior disclosure, a microdisk with a radius between 5 and 25 μm and a height between 100 and 255 nm can be excited by a nearby mono-modal straight waveguide via evanescent coupling, while a second waveguide can be used for probing the power inside the microdisk at resonance. An analyte molecule on top of the microdisk will be exposed to an evanescent field which is stronger than the field in an evanescent region of the excitation waveguide. As a result, enhancement in fluorescence emission can be obtained by the factor expressing the power inside the microdisk over the power in the excitation waveguide.

Interactions between optical waveguides and radiation emitters have been explored in the field of integrated photonics. For instance, it has been shown that high index contrast nano-photonic waveguides can excite fluorescence of molecules that reside in the tail of the waveguide mode. On the other hand, photonic crystal cavities have been shown to suppress or enhance luminescence of single radiation emitters using the Purcell effect, e.g. emitters placed in the near field of a resonant cavity emit preferentially in the cavity mode. Generally this effect scales with Q/V, with Q the quality factor of the cavity resonance and V the mode volume. Interestingly, the Purcell effect may act similarly to a filter, with the Q-factor of the resonance determining the rejection rate for non-resonant wavelengths and may promote emission in the desired mode.

SUMMARY OF THE INVENTION

Embodiments disclosed herein can provide devices, systems and methods for the study of fluorescence particle emissions, e.g. bioparticle emissions, caused by radiation stimulation.

Embodiments disclosed herein can enable single molecule fluorescence signals to be collected with high efficiency.

Embodiments disclosed herein can enable an integrated solution to be provided for performing analysis of biological processes down to the level of single particles, e.g. single molecules, in the presence of a high background. Embodiments disclosed herein can further enable accurate detection of fluorescence using a resonant coupler for coupling the radiation into an emission waveguide.

Embodiments disclosed herein can utilize a wash-free assay that may allow a measurement of biomolecular interactions in real-time.

Embodiments disclosed herein can be used in conjunction with an overall assay protocol and sample/liquid handling system.

Embodiments disclosed herein may be suitable for highly integrated devices such as handheld devices.

Embodiments disclosed herein combine spatial localization provided by excitation confinement with high index-contrast waveguide circuits.

Embodiments disclosed herein can permit different emission colors to be detected simultaneously.

Embodiments disclosed herein can achieve large scale parallelization of the detection of single molecule fluorescence can be achieved.

The above objective is accomplished by a method and device according to the present invention.

The present invention relates to an integrated waveguide structure comprising a substrate, a waveguide layer arranged on top of the substrate, the waveguide layer comprising at least one excitation waveguide for transmitting excitation radiation to activate a fluorescent particle, at least one emission waveguide, distinct from the excitation waveguide, and configured for transmitting radiation emitted by the fluorescent particle and a particle radiation coupler being a resonator element arranged for coupling radiation emitted by the fluorescent particle to the emission waveguide in response to the activation by the excitation radiation transmitted via the excitation waveguide. The waveguide structure also comprises at least one sensing site configured with respect to the at least one excitation waveguide and emission waveguide such that a fluorescent particle at the sensing site is activated by the excitation radiation transmitted via the at least one excitation waveguide and radiation emitted by the fluorescent particle is coupled into the emission waveguide by the particle radiation coupler. It is an advantage of embodiments according to the present invention that a compact system optical system can be obtained for analyzing particles such as labeled bioparticles. The fluorescent particle may be a labeled particle, e.g. labeled with a fluorophore. The particle may be a bioparticle. The sensing site may be based on or part of an oxide layer.

The waveguide structure furthermore may comprise a sensing layer arranged on top of the waveguide layer. The sensing layer may be an oxide layer.

The at least one sensing site may be on top of the sensing layer, may be on top of the waveguide layer if no sensing layer is present, may be in a cavity in the sensing layer, may be in a cavity extending through the sensing layer and extending in the waveguide layer, may be in a cavity directly made in the waveguide layer.

The at least one sensing site may be positioned with respect to the at least one excitation waveguide such as to enable the activation of the fluorescent particle by an evanescent field of the radiation propagating through the at least one excitation waveguide. It is an advantage of embodiments according to the present invention that efficient excitation can be obtained in a compact structure. The at least one excitation waveguide may be adapted for transmitting excitation radiation suitable for fluorescent activation of the fluorescent particle.

The particle radiation coupler may be any of a disk resonator, a ring resonator, a linear resonator or a photonic crystal resonator.

The particle radiation coupler may be tuned for coupling radiation having a wavelength corresponding with the wavelength of the fluorescence emission of the fluorescence particle.

The particle radiation coupler may be positioned in the emission waveguide or in the near field thereof. The sensing site may be located above the eat least one emissive waveguide.

The particle radiation coupler may be a resonator element positioned in between the at least one emission waveguide and the at least one excitation waveguide and in which the at least one sensing site is positioned in between the excitation waveguide and the resonator element. The resonator element can in one example comprise a disk resonator element.

The at least one excitation waveguide may be connected to the at least one emission waveguide, and the particle radiation coupler may be a resonator element formed in the at least one emission waveguide. The sensing site may be located above the at least one emission waveguide. The resonator element may comprise at least one photonic crystal cavity. It is an advantage of embodiments of the present invention that a compact system can be obtained.

The direction of the at least one excitation waveguide may be substantially orthogonal to the direction of the at least one emission waveguide. It is an advantage of embodiments of the present invention that by positioning the waveguides orthogonally optimal separation between excitation and emission radiation can be obtained thus resulting in reduced excitation radiation disturbing the detection. Furthermore, such orthogonally positioning may allow using a plurality of excitation and emission waveguides such that a high density of sensing sites can be obtained.

The at least one excitation waveguide and the at least one emission waveguide thus may form crossing waveguides.

The sensing site may be positioned above or in the emission waveguide, away from the center of the crossing waveguides. The sensing site may be positioned above or in the emission waveguide and the sensing site may be positioned off-center with respect to the excitation waveguide.

The excitation waveguide may comprise a mode expander, whereby the mode expander is positioned at or near the sensing site so that excitation radiation at the position of the mode expander can excite the fluorescent particle.

The at least one excitation waveguide may comprise a plurality of substantially parallel excitation waveguides. The at least one emission waveguide may comprise a plurality of substantially parallel emission waveguides, crossing the plurality of substantially parallel excitation waveguides, and a plurality of sensing sites may be provided, each sensing site being located at a crossing of an excitation waveguide and an emission waveguide. It is an advantage of embodiments of the present invention that a compact device is provided allowing parallel detection of a plurality of fluorescent particles simultaneously. It is an advantage of embodiments according to the present invention that a high density of different sensing sites can be obtained.

The at least one sensing site may have a surface chemistry adapted for capturing the fluorescent particle. The sensing site may comprise a cavity. It is an advantage of embodiments according to the present invention that accurate positioning of the particle to be sensed can be performed.

The cavity may have a size which is smaller than the wavelength of the radiation transmitted by the excitation waveguide. It is an advantage of embodiments according to the present invention that good excitation of the particle to be sensed may be obtained. The cavity size may in some embodiments be smaller than 800 nm, e.g. smaller than 600 nm, e.g. smaller than 400 nm. The waveguide structure may be operational in the range 400 nm to 800 nm.

The present invention also relates to a characterization system for characterizing at least one fluorescent particle, the characterization system comprising at least one waveguide structure as described above, at least one excitation radiation source for transmitting excitation radiation through the at least one excitation waveguide of the at least one waveguide structure, and at least one detector for detecting radiation transmitted by the at least one emission waveguide of the at least one waveguide structure. It is an advantage of embodiments according to the present invention that the waveguide structure as described above can be easily combined, in an integrated homogeneous and/or heterogeneous manner or in a non-integrated manner, with excitation and detection facilities so as to form a compact and efficient detection system. The at least one detector may be a spectral detector.

The at least one detector may be an integrated detector integrated in the at least one emission waveguide and/or wherein the at least one radiation source may be an integrated radiation source integrated in the at least one excitation waveguide. The system may comprise butt couplers or grating couplers for coupling excitation radiation into the excitation waveguide and/or out of the emission waveguide.

The at least one detector may comprise a rejection filter suitable for rejecting excitation radiation transmitted by the excitation waveguide. It is an advantage of embodiments according to the present invention that additional measures for further preventing the detection from being disturbed by excitation radiation can easily be taken. It is an advantage of embodiments of the present invention that thus more accurate detection can be obtained.

The integrated waveguide structure may comprise a plurality of substantially parallel excitation waveguides and a plurality of substantially parallel emission waveguides, crossing the plurality of substantially parallel excitation waveguides, and wherein a plurality of sensing sites are provided, each sensing site being located at a crossing of an excitation waveguide and an emission waveguide, the system comprising excitation facilities for each of the substantially parallel emission waveguides and detection facilities for each of the emission waveguides, the system furthermore comprising a controller programmed for sequentially activating different sets of fluorescence particles by sequentially transmitting excitation radiation in the excitation waveguides. It is an advantage that a compact detection system for analyzing a plurality of particles can be obtained whereby the number of sensing sites per area can be high. It is an advantage of embodiments according to the present invention that efficient and fast measurement, simultaneously for a number of sensing sites, can be performed.

The system may be adapted for transmitting excitation radiation in the excitation waveguides by sweeping an excitation beam sequentially over a set of excitation radiation coupling elements for sequentially coupling excitation radiation into the excitation waveguides.

The characterization system may comprise a chemical cell. The chemical cell may comprise two reservoirs separated by a membrane whereby the two reservoirs can be connected through a nanopore in the membrane. One of the reservoirs may comprise ion-sensitive fluorescent dyes and the other reservoir may comprise ions influencing the fluorescent dyes. Such ions may be Calcium ions. The chemical cell furthermore may comprise an electric field generating means for inducing an electric field over the membrane for inducing an ion flow towards the reservoir with the ion-sensitive fluorescent dyes.

The waveguide structure may be arranged such that the sensing site is sensing the ion-sensitive fluorescent dyes influenced by ion flow. The detector may be adapted for detecting a variation in the fluorescence of the ion-sensitive fluorescent dyes.

The waveguide structure may form the membrane, or in other words, the membrane may be formed by the waveguide structure.

One example embodiment relates to a method for characterizing at least one fluorescent particle, the method comprising transmitting excitation radiation into at least one excitation waveguide of an integrated waveguide structure, activating the fluorescent particle positioned at a sensing site of the integrated waveguide structure, the sensing site being configured such that a fluorescent particle at the sensing site is activated by the excitation radiation transmitted via the at least one excitation waveguide (101) and radiation emitted by the fluorescent particle is coupled into the emission waveguide (102, coupling radiation emitted by the fluorescent particle to an emission waveguide of the integrated waveguide structure, the emission being distinct from the excitation waveguide, and detecting radiation emitted by the fluorescent particle and transmitted via the emission waveguide. In one embodiment, the method may comprise analyzing a plurality of particles using an integrated waveguide structure comprising a plurality of substantially parallel excitation waveguides and a plurality of substantially parallel emission waveguides, crossing the plurality of substantially parallel excitation waveguides, and wherein a plurality of sensing sites are provided, each sensing site being located at a crossing of an excitation waveguide and an emission waveguide, the method comprising simultaneously activating a plurality of fluorescence particles positioned at sensing sites located at the same excitation waveguide, coupling radiation emitted by these fluorescent particles to the plurality of emission waveguides located at the sensing sites and simultaneously detecting the radiation transmitted via the respective emission waveguides. The method also may comprise activating different sets of fluorescence particles sequentially by sequentially transmitting excitation radiation in the excitation waveguides.

In some embodiments, the fluorescent particles may be ion-sensitive fluorescent dyes, the method furthermore comprising, generating an ion flow through a nanopore of a membrane towards ion-sensitive fluorescent dyes positioned at the sensing site, performing said transmitting, said activating, said coupling and said detecting, and deriving, based on said detecting, a point in time that the ion flow is reduced representative for a particle translocating the pore and blocking the ion flow. Some embodiments also relate to the use of a system as described above for any of sequencing DNA or detecting a bioparticle.

Particular aspects are set out in the accompanying independent and dependent claims. In alternate embodiments, features from the dependent claims may be combined with features of the independent claims and with features of other dependent claims as appropriate and not merely as explicitly set out in the claims.

These and other aspects will be apparent from and elucidated with reference to the embodiment(s) described hereinafter.

BRIEF DESCRIPTION OF THE DRAWINGS

FIG. 9 shows a system according to embodiments of the present invention comprising a movable radiation source and grating couplers.

FIG. 10 shows a combination of resonators to couple out selective portions of the spectrum into separate detectors in a system according to embodiments of the present invention.

FIG. 11 shows a method according to embodiments of the present invention.

Figure 1:
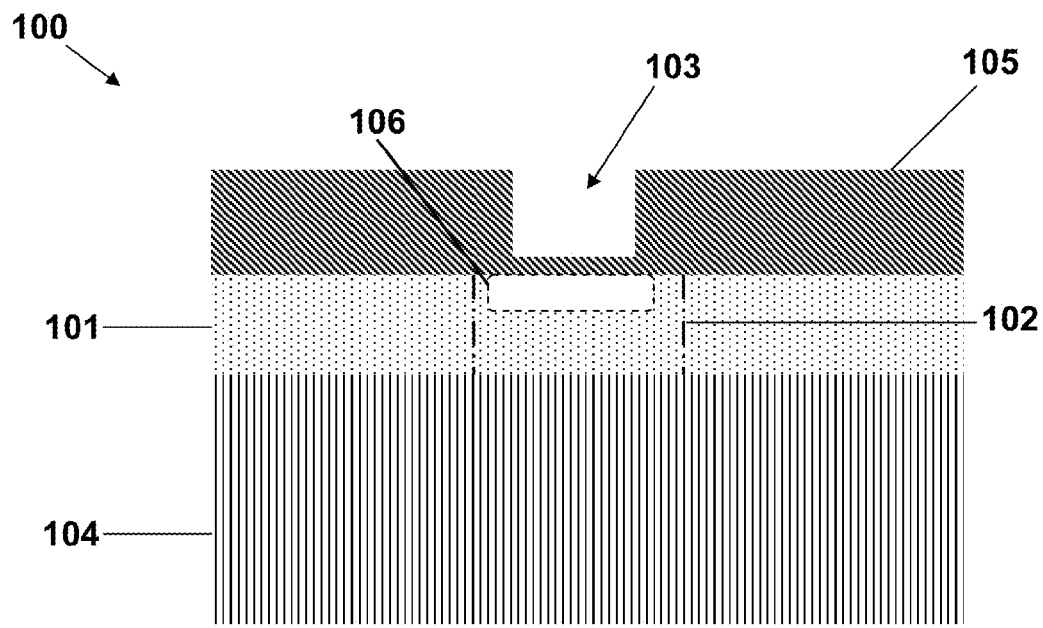
FIG. 1 shows a waveguide structure according to embodiments of the first aspect of the invention.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Some embodiments described herein may combine spatial localization of the emission of a bioparticle being analyzed, e.g. provided by confinement of the excitation in a sensing site, with waveguide circuits that fulfil the role of both excitation and collection, for example high index-contrast waveguide circuits. For example, the sensing site may comprise a cavity. The sensing site may thus be formed by a nano-aperture, e.g. a nano-aperture provided in the oxide layer. Furthermore, by engineering a high quality factor resonant structure near the nano-aperture, e.g. around the nano-aperture, a single molecule fluorescence signal can be collected with high efficiency. Furthermore, different colours may be detected simultaneously in various embodiments. By integration of excitation and detection on a single chip, in accordance with certain embodiments, large scale parallelization of the detection of single molecule fluorescence can be achieved. In some embodiments, this parallelization can be increased even more by integrating the detectors on the photonic chip. For example, a device according to embodiments may enable real-time observation of the binding of fluorescent-dye-labelled antibodies to protein receptors at the surface of a cell membrane.

A photonics-on-chip platform according to embodiments of the present invention may provide efficient excitation and detection of single molecule fluorescence (SMF). Embodiments may provide good collection of the low signals generated by SMF on chip by limiting noise sources and photon losses. A system according to embodiments of the present invention may be particularly suitable for research applications such as sequencing, proteomics and cell biology, as well as for providing a simple and low cost alternative for immunoassays in point of care systems. The ability to sense binding in a high background allows to develop wash-free assays as well as to sense responses in real-time and measure binding kinetics. Thus, embodiments of the present invention may advantageously provide miniaturization of integration and may be applied in fast, wash-free portable sensing devices.

The structures according to embodiments of the present invention will refer to a waveguide layer on top of a substrate. In embodiments of the present invention, the term "substrate" may include any underlying material or materials that may be used, or upon which a device, a circuit or an epitaxial layer may be formed. In other alternative embodiments, this "substrate" may include a semiconductor substrate such as e.g. doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or a $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest. Also, the "substrate" may be any other base on which a layer is formed, for example a glass or metal layer.

According to some embodiments, the waveguide structure as will be described may be implemented as a photonics integrated circuits. This refers to a variety of forms and material systems such as for example low-index contrast waveguide platforms (e.g. polymer waveguides, glass/silica waveguides, $Al_xGa_{1-x}As$ waveguides, $In_xGa_{1-x}As_yP_{1-y}$ waveguides), high-index contrast waveguides (e.g. Silicon-on-Insulator, semiconductor membranes), plasmonic waveguides (e.g. metal nano-particle arrays, metal layers), also called Photonic Lightwave circuits (PLC). According to particular embodiments, the sensing systems could be implemented in a silicon-on-insulator platform. The high refractive index contrast allows photonic waveguides and waveguide components with submicron dimensions to guide, bend and control light on a very small scale so that various functions can be integrated on a chip. Moreover SOI offers a flexible platform for integration of resonator elements which in turn allows for even higher levels of miniaturization. Using Silicon-on-insulator also has some technological advantages. Due to the CMOS industry, silicon technology has reached a level of maturity that outperforms any other plane chip manufacturing technique by several orders of magnitude in terms of performance, reproducibility and throughput.

In a first aspect, the present invention relates to an integrated waveguide structure which comprises a substrate, a waveguide layer arranged on top of the substrate and a sensing site. The waveguide layer comprises at least one excitation waveguide for transmitting radiation for activating a fluorescent particle, e.g. a fluorescent label of a bioparticle. The waveguide layer also comprises at least one emission waveguide for transmitting radiation emitted by the label of the bioparticle, the emission waveguide being distinct from the emission waveguide. The structure also comprises a particle radiation coupler, the coupler being a resonator, for coupling radiation emitted by the fluorescent particle to the emission waveguide in response to the activation by radiation transmitted via the excitation waveguide. As indicated the fluorescent particle may be a labelled bioparticle whereby the label comprises a fluorescent tag, e.g. may comprise a fluorophore, which is chemically or physically attached to the bioparticle. The bioparticle may comprise a molecule or biological entity of interest, e.g. attached to a DNA molecule, a protein, a cell organelle or a biological cell. The sensing site is configured with respect to the at least one excitation waveguide and emission waveguide such that a fluorescent particle at the sensing site is activated by excitation radiation transmitted via the excitation waveguide, e.g. such as to enable the direct activation of the label of the bioparticle by radiation transmitted via the excitation waveguide. The sensing site is also configured such that the radiation emitted by the fluorescence particle is coupled into the emission waveguide by the particle radiation coupler. Several configurations are possible. For example, the sensing site may be positioned such as to enable the activation of the label of the bioparticle by the evanescent field of the radiation propagating through the excitation waveguide. Alternatively also direct excitation is possible. The sensing site may be on top of or being part of a sensing layer, it may be in a cavity in the sensing layer, in a cavity reaching through the sensing layer and into the waveguide layer, it may be in a cavity reaching through the waveguide layer.

The waveguide structure according to embodiments of the present invention can be used in a sequencing architecture for detecting radiation emitted by fluorescent tags of molecules. The optical waveguides in the waveguide structure may conduct radiation for exciting molecules, e.g. fluorescent tags, and conduct radiation emitted by these molecules for detection. For example, a sequencing architecture comprising such waveguide structures may comprise a plurality of unit cells, in which each unit cell is formed at a crossing of optical waveguides.

Referring to FIG. 1, a waveguide structure 100 according to embodiments of this first aspect of the invention is shown.

The integrated waveguide structure comprises a substrate 104, e.g. a semiconductor substrate, e.g. a silicon substrate. For example, the integrated waveguide structure may be processed on the substrate using a photonic semiconductor processing technology, e.g. silicon-on-insulator (SOI) processing. On this substrate 104, a waveguide layer is arranged which comprises at least one excitation waveguide 101 for transmitting radiation for activating a label of a bioparticle. For example, the waveguide 101 may be adapted in material composition and structure to allow propagation of a radiation wave comprising a spectral wavelength component attuned to an activation wavelength of the label of the bioparticle. The label of the bioparticle may be a fluorescent label, e.g. a fluorophore component attached to the bioparticle, and the excitation waveguide may be adapted for transmitting radiation suitable for activating the fluorescent label.

The at least one excitation waveguide 101 may be adapted for efficient excitation of the bioparticle in a narrow region above the waveguide, such that excitation of the bioparticle at the sensing site is obtained while limiting background emissions, e.g. fluorescence of other diffusing molecules outside the target volume defined by the sensing site. The design of the excitation waveguide 101 may furthermore be adapted for limiting autoluminescence. For example, the radiation power coupled into the waveguide core can be limited to reduce potential effects of autoluminescence. The extent of the tail of the waveguide mode can strongly depend on the mode confinement, thus a suitable material composition and cladding material may be chosen for obtaining advantageous properties. For example, the excitation waveguide 101 may be a SiN or $TiO_2$ waveguide with a $SiO_2$ cladding. The excitation waveguide 101 may furthermore be excited using butt coupling or by employing diffraction gratings combined with optical fibers.

Figure 23:
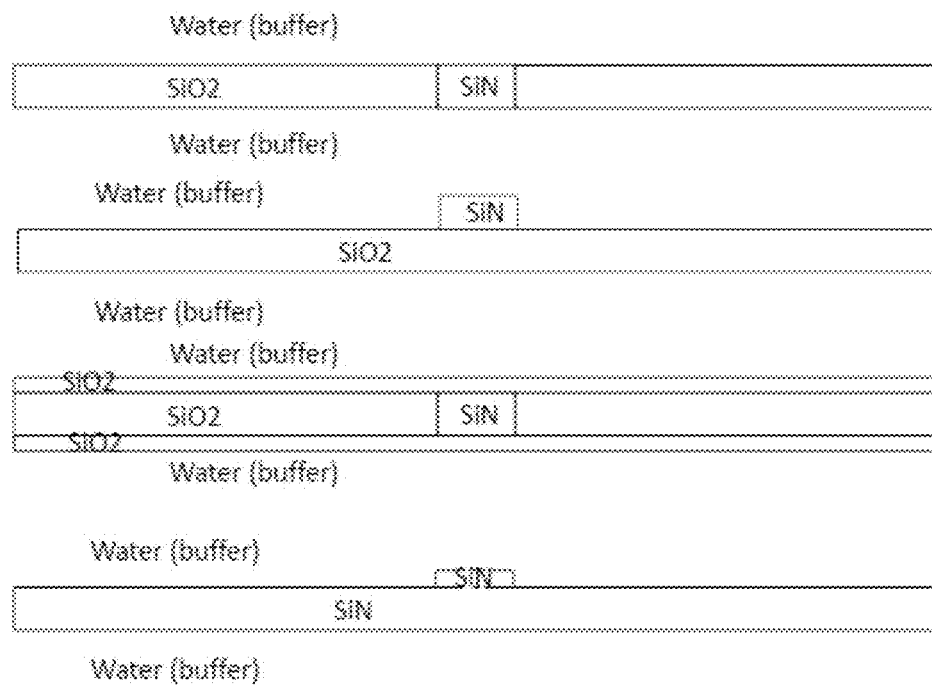
FIG. 23 illustrates possible waveguide cross-sections as can be used in embodiments of the present invention.

By way of illustration, a number of possible cross sections is shown in FIG. 23.

The waveguide layer further comprises at least one emission waveguide 102 for transmitting radiation emitted by the label of the bioparticle and a particle radiation coupler, e.g. resonator 106, for coupling radiation emitted by the label of the bioparticle to the emission waveguide in response to the activation by radiation transmitted via the excitation waveguide 101. For example, the emission waveguide 102 may be a SiN or $TiO_2$ waveguide with a $SiO_2$ cladding. The emission waveguide 102 may furthermore be coupled to a detector for registering the radiation emitted by the label of the bioparticle. Embodiments of the present invention may advantageously combine a far-field excitation of labelled bioparticles with near-field collection of the emitted radiation.

The interaction between the particle radiation coupler 106 for coupling radiation emitted by the label of the bioparticle to the emission waveguide and the emitted radiation, e.g. by fluorescence, may provide a high coupling efficiency. For example, the resonator may be adapted to provide a high coupling efficiency for different polarizations of the emitted fluorescence photons, for the different wavelengths within the spectral emission band of the chosen labels, e.g. fluorescence dyes, and for varying positions of the bio-particle at the sensing site, e.g. in the nano-aperture. The coupler design may thus be adjusted to the intended use by applying standard experimentation and numerical simulation, e.g. by performing finite difference time domain or finite element simulations, which are conventional means for optimization known in the art. The particle radiation coupler may be selected so that the resonant wavelength is matched with the fluorescent emission spectrum. Also the total spectral overlap between the emission spectrum and the "enhanced"

resonance line may be matched. Resonators with multiple resonances in the emission spectrum may be selected as these typically may perform better than a resonator with a single, very narrow line. The particle radiation coupler may be a photonic crystal coupler, a disk resonator, a linear resonator, a ring resonator, etc. The coupler may be a resonator 106 comprising a one-dimensional (1D) photonic crystal resonators, as discussed further below in an exemplary embodiment. In such 1D photonic crystal resonator, a cavity is created in a regular strip waveguide, e.g. the emission waveguide, by combining Bragg mirrors with a central cavity. Very high Q factors have been demonstrated for this type of cavity in Si photonics. Alternatively, the resonator 106 may comprise a disk resonator coupled to the emission waveguide, e.g. a strip waveguide, as also discussed further below in an exemplary embodiment. The disk resonator may be positioned within the near field of the emission waveguide to achieve good coupling. Also for these types of resonators, high Q factors have been demonstrated in the art for coupling to emitters, although mainly for near-infrared wavelengths. The resonance wavelength of the resonator 106, e.g. the photonic crystal cavities or the disk resonator, may be tuned to a predetermined range, e.g. in the visible part of the spectrum, for example between 600 and 700 nm, while conserving a high resonance Q-factor.

Furthermore, the emission waveguide 102 may be adapted for supporting one or multiple modes. For example, the collection of multiple emission lines can be achieved in corresponding modes, which can be advantageous in various applications, e.g. for biological assays. The resonator 106 may also be adapted for allowing multiple modes, with a spectral spacing given by the free spectral range.

The integrated waveguide structure also may comprise a sensing layer, e.g. an oxide layer. Such a layer may be arranged atop the waveguide layer. The sensing site 103, being part of the integrated waveguide structure, may be position in or at the sensing layer, if the sensing layer is present. The oxide sensing layer thus may comprise the sensing site 103 and the sensing site may be adapted for capturing the bioparticle. This sensing site is positioned such as to enable the activation of the label of the bioparticle by radiation transmitted via the excitation waveguide. The sensing site 103 may have a surface chemistry adapted for capturing the bioparticle, for example may comprise a biological molecule suitable for capturing the bioparticle. The surface of the sensor may be modified by a coating which is designed to attract certain molecules or may be modified by attaching molecules to it, which are suitable to bind the target molecules which are present in the sample fluid. Such molecules are know to the skilled person and include complementary DNA, antibodies, antisense RNA, etc. Such molecules may be attached to the surface by means of spacer or linker molecules. The surface can also be provided with molecules in the form of organisms (e.g. viruses or cells) or fractions of organisms (e.g. tissue fractions, cell fractions, membranes). The sensing site 103 may in one example comprise a cavity, e.g. a cavity having a size which is smaller than the wavelength of the radiation transmitted by the excitation waveguide 101. The sensing site may for example be a nano-aperture, e.g. defined by applying electron beam lithography (EBL) to the sensing layer, e.g. oxide layer.

Figure 3:
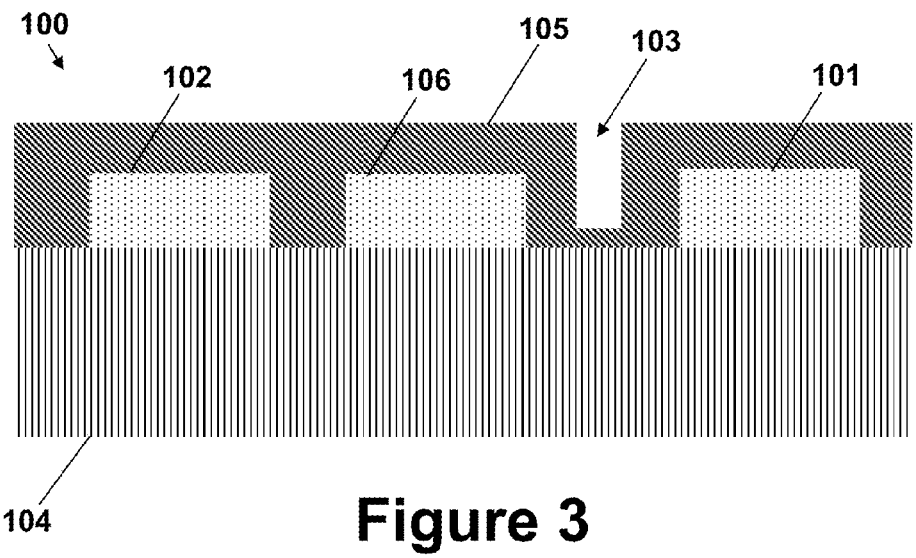
FIG. 3 shows a layer cross-section of a waveguide structure according to a first exemplary embodiment of the first aspect of the present invention, which comprises a disk resonator.
Figure 4:
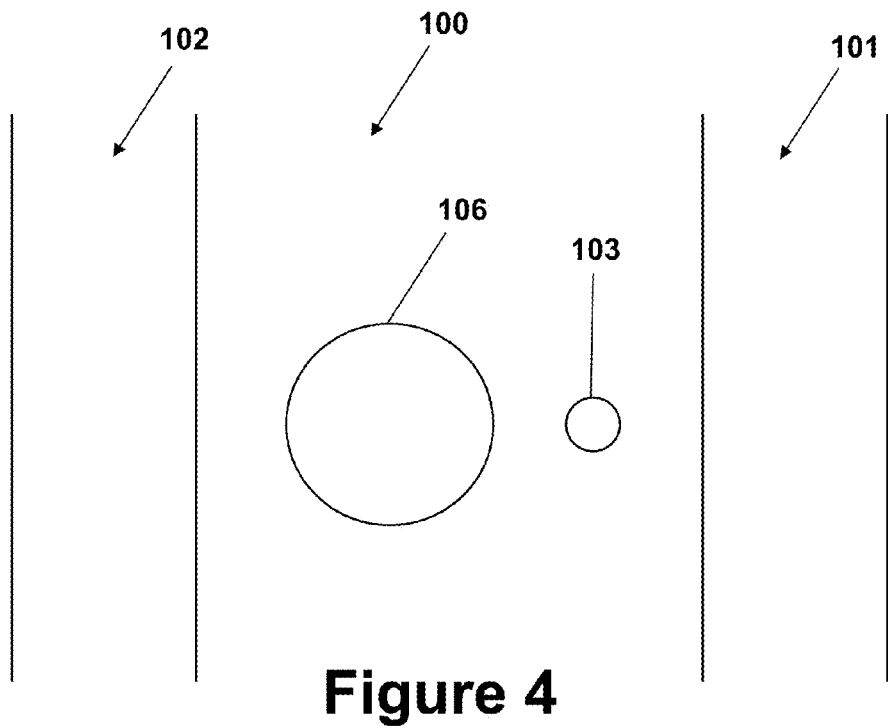
FIG. 4 shows a top-view projection of a waveguide structure according to the first exemplary embodiment of the first aspect of the present invention.
Figure 5:
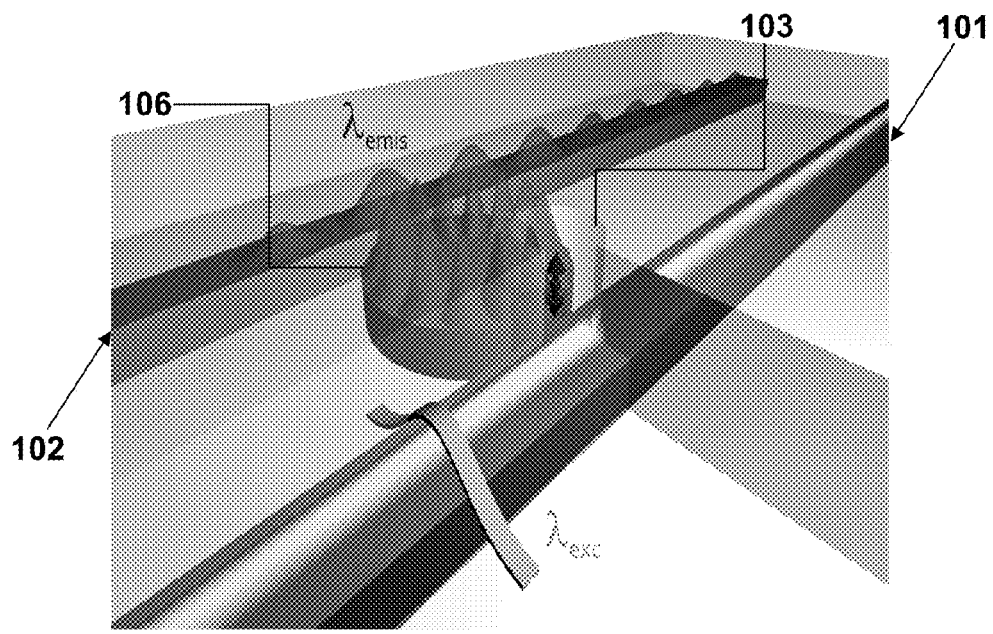
FIG. 5 shows a three-dimensional model rendering of a waveguide structure according to the first exemplary embodiment of the first aspect of the present invention.

In a waveguide structure 100 according to a first embodiment, shown in FIG. 3 to FIG. 5, the coupler 106 is a resonator 106 positioned in between the emission waveguide 102 and the excitation waveguide 101 and the sensing site 103 is positioned in between the excitation waveguide 101 and the resonator 106. For example, the resonator 106 may be positioned such that the orthogonal projection of the resonator onto the plane of the substrate 104 lies between the orthogonal projection of the emission waveguide 102 onto the plane of the substrate 104 and the orthogonal projection of the excitation waveguide 101 onto the plane of the substrate 104. Likewise, the sensing site 103 may be positioned such that the orthogonal projection of the position of the sensing site 103 onto the plane of the substrate lies between the orthogonal projection of the excitation waveguide 101 onto the plane of the substrate 104 and the orthogonal projection of the resonator 106 onto the plane of the substrate. The resonator may be a disk resonator, although embodiments are not limited thereto and may for example also be linear resonators, ring resonators, photonic crystal resonators, etc.

FIG. 5 furthermore shows a three-dimensional model rendering of a waveguide structure according to this first embodiment. The resonator, microdisk resonator 106 in the particular example, may couple the emission radiation $\lambda_{emis}$ emitted by the fluorescence particle to the emission waveguide. The bio-particle may be excited by radiation $\lambda_{exc}$ from the excitation waveguide in the nano-aperture that couples the emission to the cavity resonance, e.g. the evanescent field of radiation transmitted through the excitation waveguide may induce fluorescence of the label of the bioparticle.

Figure 6:
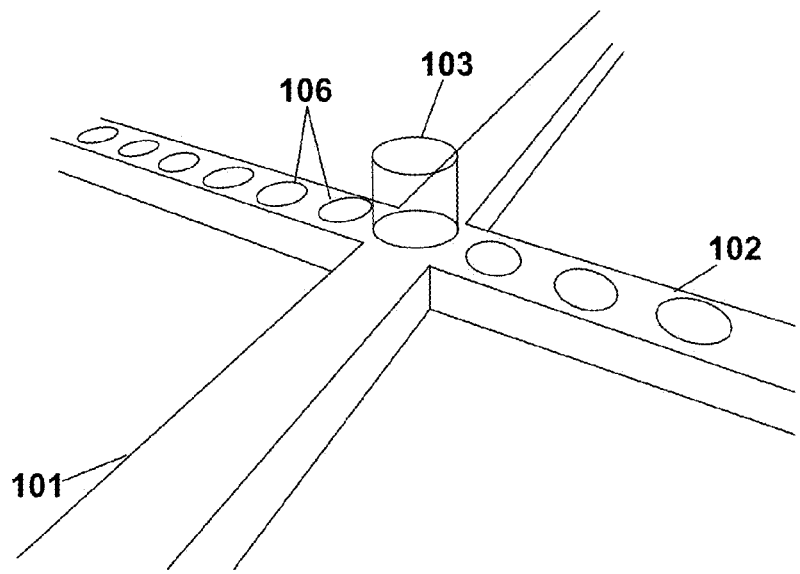
FIG. 6 shows a waveguide structure according to a second exemplary embodiment of the first aspect of the invention, in which the excitation waveguide may be connected to the emission waveguide in a cross junction and which comprises at least one photonic crystal cavity formed in the emission waveguide.
Figure 7:
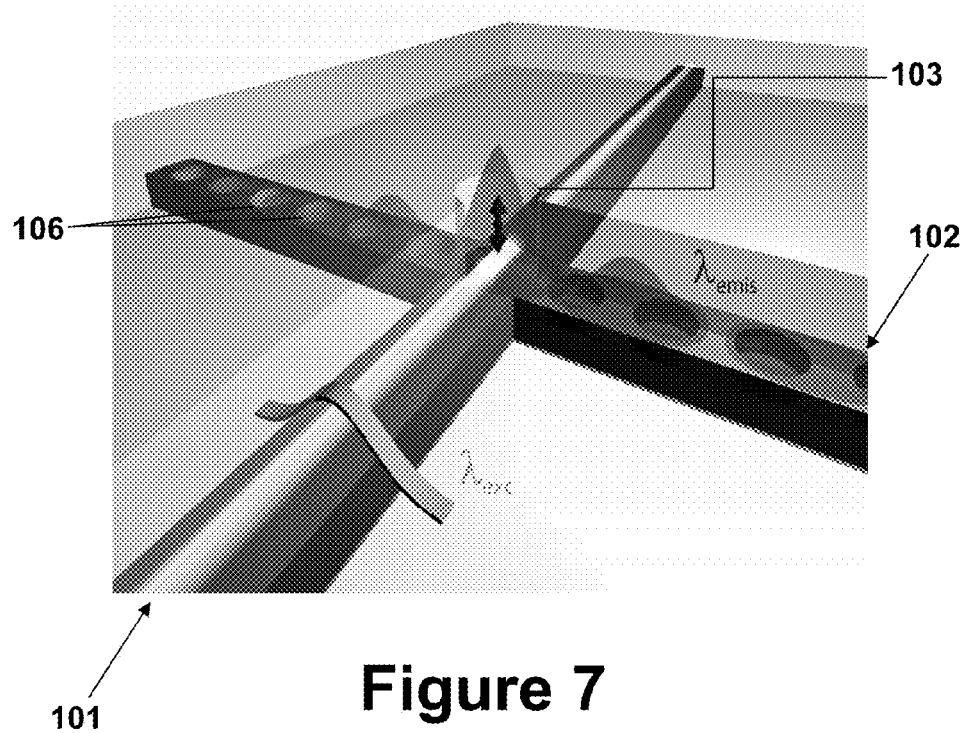
FIG. 7 shows a three-dimensional model rendering of the waveguide structure according to the second exemplary embodiment of the first aspect of the present invention.

In a waveguide structure 100 according to a second embodiment, shown in FIG. 6 and FIG. 7, the excitation waveguide 101 may be connected to the emission waveguide 102, e.g. the waveguide layer may comprise a cross junction at the intersection of the excitation waveguide 101 and the emission waveguide 102. In this embodiment, the resonator 106 may comprise at least one photonic crystal cavity formed in the emission waveguide 102. The sensing site 103 may furthermore be located above the emission waveguide 102, e.g. the emission waveguide 102 may lay between the sensing site 103 and the substrate along a direction orthogonal to the plane of the substrate. In such embodiment, the direction of the excitation waveguide 101 and the direction of the emission waveguide 102 may be substantially orthogonal, e.g. may be orthogonal. For example, the angle between the direction of the excitation waveguide 101 and the emission waveguide 102 may be in the range of 80° to 100°, e.g. preferably in the range of 85° to 95°.

The spacing between the sensing site and the excitation and emission waveguide spacing may be chosen such that coupling for excitation and collection are achieved. The crossed waveguide combination can provide a geometry to achieve a substantial coupling efficiency.

The sensing site also may be positioned in a cavity in the sensing layer, in a cavity in the waveguide layer or in a cavity extending through the sensing layer and the waveguide layer.

FIG. 7 shows a three-dimensional model rendering of a waveguide structure according to this second embodiment. The photonic crystal cavity resonator 106 may couple the emission radiation $\lambda_{emis}$ emitted by the label of the bioparticle to the emission waveguide. The bio-particle may be excited by radiation $\lambda_{exc}$ from the excitation waveguide at the sensing site 103, e.g. in the nano-aperture that couples the emission to the photonic crystal cavity resonance.

Figure 2:
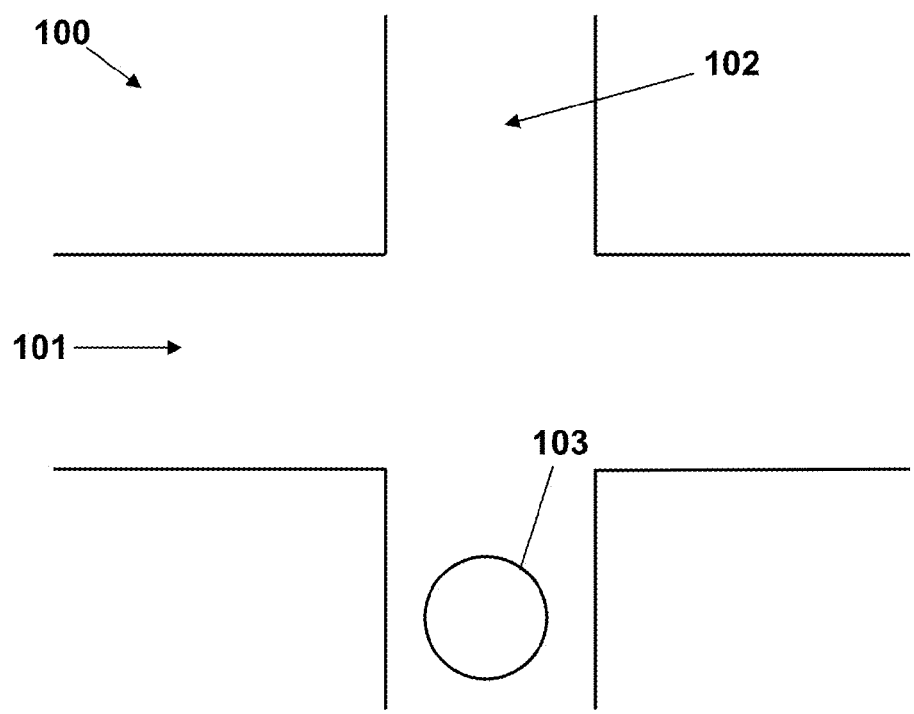
FIG. 2 shows an orthogonal arrangement of the emission waveguide and the excitation waveguide in a waveguide structure according to embodiments of the present invention.

For example, as shown in FIG. 2, the horizontal waveguide may be employed as the excitation waveguide 101, while the vertical waveguide may act as the emission waveguide 102. In operation, the bioparticle can attach to the sensing site 103, which may be located near the emission waveguide 102. When a radiation wave propagates through the excitation waveguide 101, distortion of the excitation wave may be limited by locating the sensing site away from the crossing of the optical waveguides. The label of the bioparticle at the sensing site may be activated by the evanescent field of the radiation propagating through the excitation waveguide, e.g. the tail of the excitation radiation wave may enter the emission waveguide slightly to activate the fluorescent tag of the molecule. The emitted radiation of the tag may then be guided by the emission waveguide to a detector.

Figure 12:
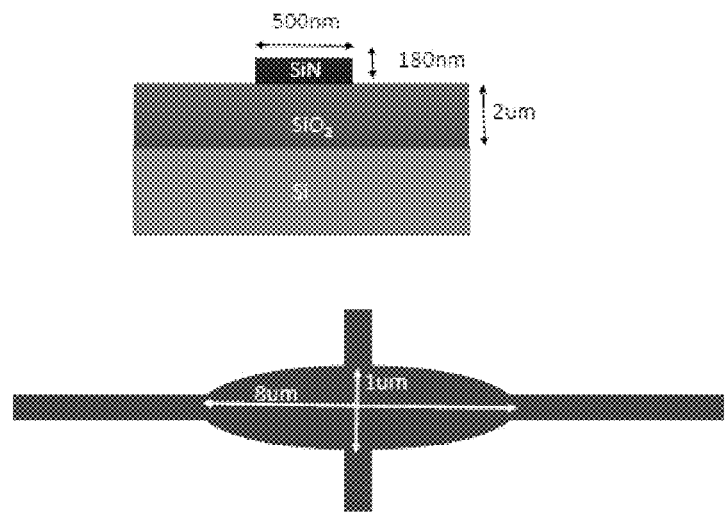
FIG. 12 illustrates a schematic example of a waveguide structure having a mode expander, according to an embodiment of the present invention.
Figure 13:
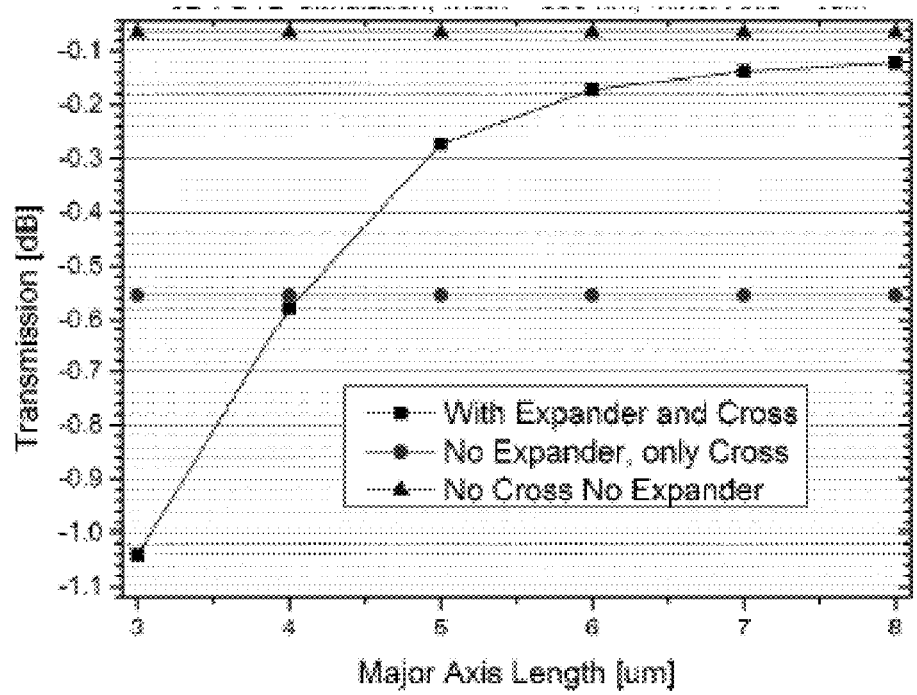
FIG. 13 illustrates simulation results for a waveguide structure comprising a mode expander, illustrating advantages of embodiments of the present invention.
Figure 14:
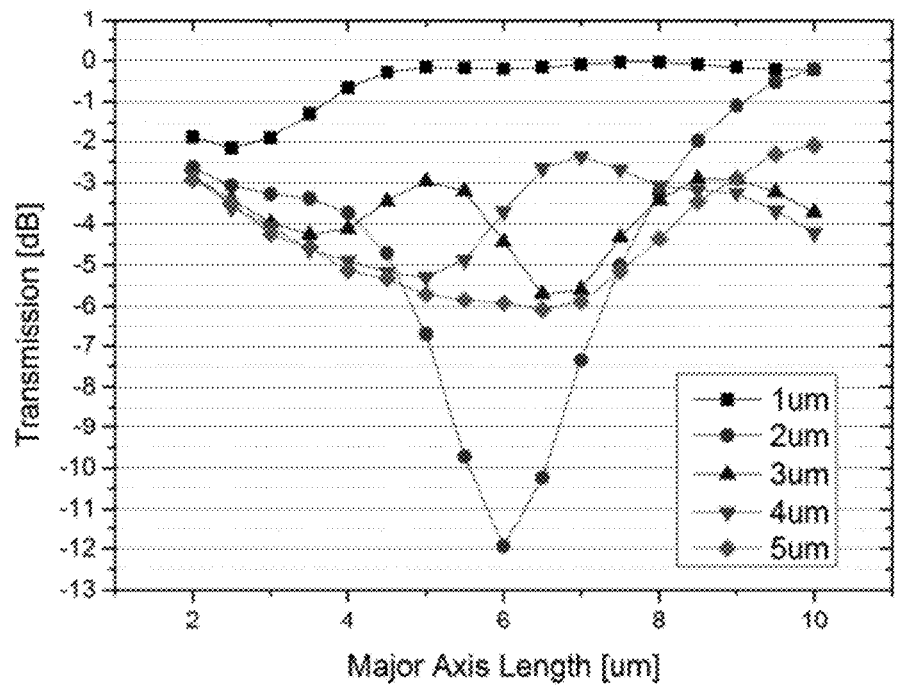
FIG. 14 illustrates the transmission as function of the major axis length for different minor axis lengths, thus illustrating advantages of embodiments of the present invention.

In some embodiments where crossing waveguides are used, the excitation waveguide may be provided with a beam expander at the position of the cross junction of the waveguides. Such an expander may result in a reduced loss at the cross-junction of the waveguides, and thus result in an advantageous structure. FIG. 12 illustrates an example of a waveguide structure wherein the excitation waveguide has a mode expander. The mode expander of the present example has an elliptical shape. In the particular example shown, the waveguide material is SiN, the waveguide height is about 180 nm high and the waveguide width is 500 nm. The waveguide structure comprises a stack of Si and 2 µm $SiO_2$ cladding layer as a substrate. The upper cladding used, although not shown, also was $SiO_2$ and the environment was water. The excitation wavelength used is 670 nm. The expander minor axis has a length of 1 µm whereas the expander major axis has a length of 8 µm. The hole diameter of the hole (not shown) in the sensing layer was selected at 150 nm. The effect of using a mode expander is shown in FIG. 13 and FIG. 14. FIG. 13 illustrates simulation results of a 3D FDTD simulation for a waveguide having a width of 500 nm and a minor axis with a length 1 µm. The transmission is shown as function of the major Axis length for a waveguide structure as shown in FIG. 13 (indicated with squares) and compared with a situation where there are crossing waveguides without mode expander (disks) as well as with a situation where no mode expander and no crossing waveguide is present. It can be seen that for a sufficiently large major axis, the losses are limited and the situation resembles much more that of a waveguide that is not crossed. From the intensity profiles it could clearly be seen that the mode expander actually also expands the mode. FIG. 14 illustrates the transmission as function of the major axis length for different lengths of the minor axis. The different lengths of the minor axis used are indicated in the legend of the drawing.

Figure 15:
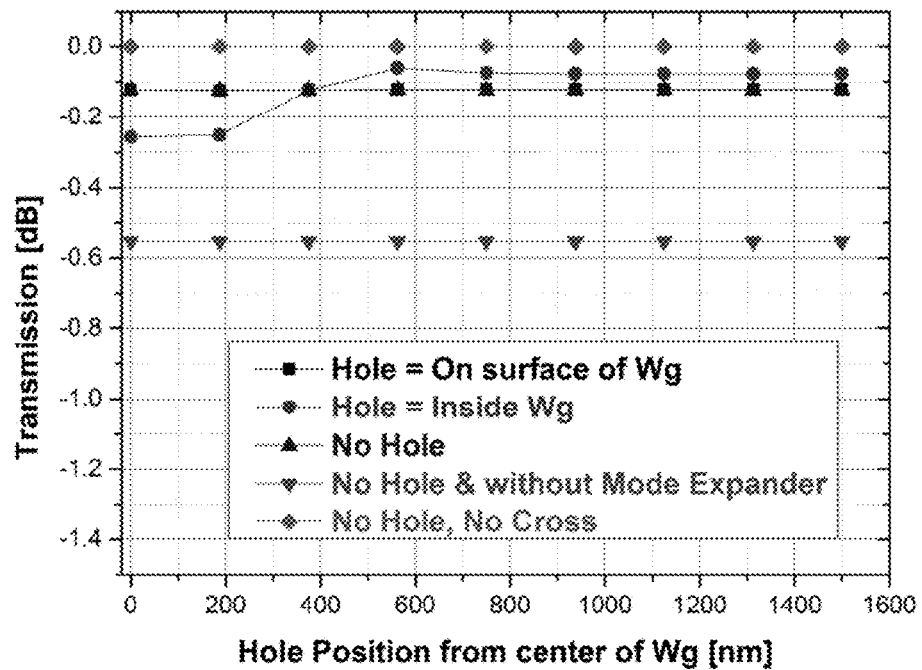
FIG. 15 illustrates the effect of the presence of a hole on the loss as function of the position of the hole from the center, thus illustrating advantages of specific embodiment of the present invention.

In some embodiments, where crossing waveguides are used, a hole (cavity) wherein the sensing site can be positioned is evaluated. The hole can extend in the sensing layer but not reaching through the waveguide layer, or it can extend through the sensing layer and the waveguide layer. Alternatively, if no sensing layer is present, it could be positioned directly in the waveguide layer. FIG. 15 illustrates the effect of the presence of the hole on the loss (how much is transmitted) as function of the position of the hole from the center of the waveguide. The situation is shown for a waveguide structure where a hole was present on the surface of the waveguide (squares) together with an expander, a hole was present inside the waveguide (disks) together with an expander, a waveguide structure without hole (triangle with point up) but with expander, a waveguide structure without hole and without mode expander (triangle with point down) and, as a reference, a waveguide structure where no hole and no crossing waveguide was present. The other parameters of the waveguide structure evaluated are as follows: the waveguide material is SiN, the waveguide height is about 180 nm high and the waveguide width is 500 nm. The waveguide structure comprises a stack of Si and 2 µm $SiO_2$ cladding layer as a substrate. The upper cladding used also was $SiO_2$ and the environment was water. The excitation wavelength used is 670 nm. The expander (if present) has an expander minor axis has a length of 1 µm whereas the expander major axis has a length of 8 µm. The hole diameter of the hole in the sensing layer was selected at 150 nm.

Figure 16:
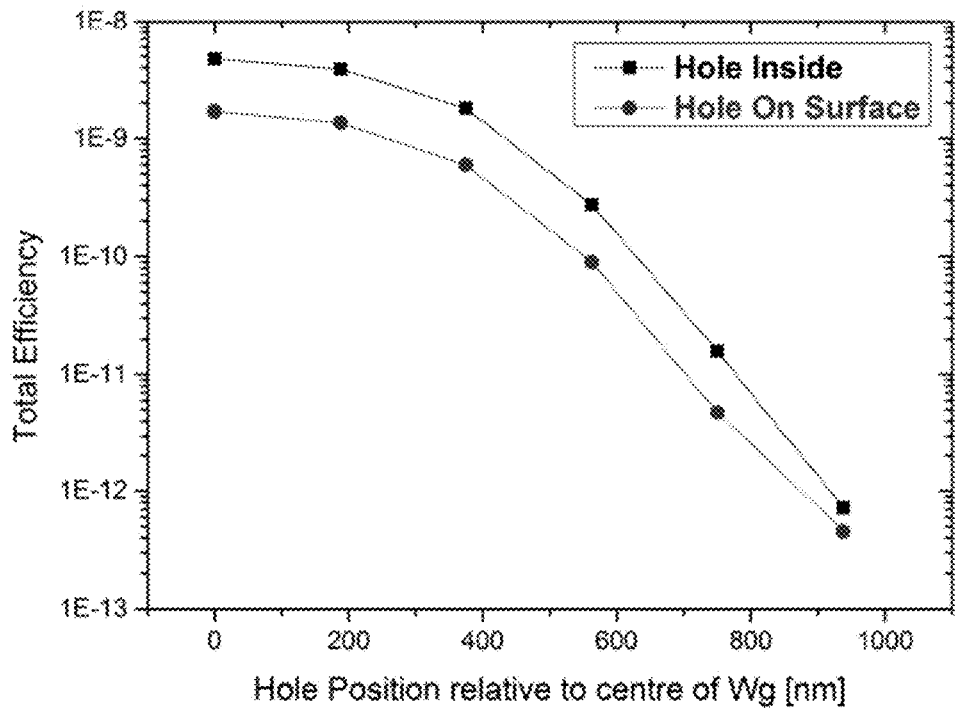
FIG. 16 illustrates the total efficiency of the waveguide structure with a hole inside the waveguide and a hole above the waveguide, according to embodiment of the present invention.
Figure 17A:
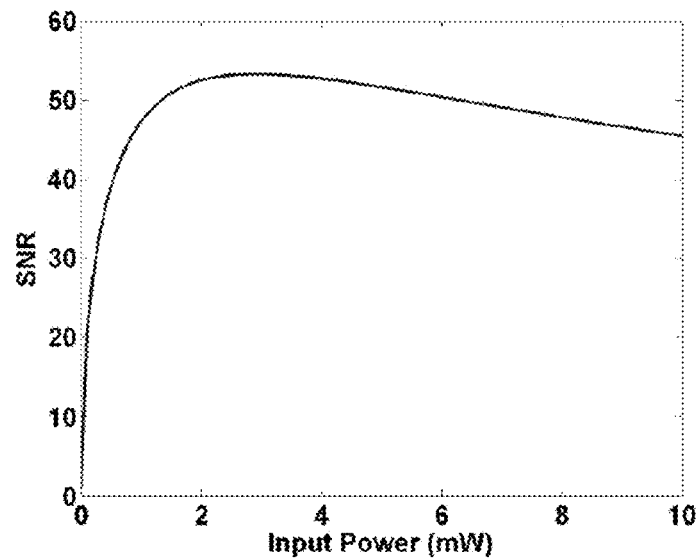
FIG. 17a to FIG. 18f illustrate the signal to noise ratio for different structures having a hole off-axis in the waveguide, thus illustrating features and advantages of embodiments of the present invention.
Figure 17B:
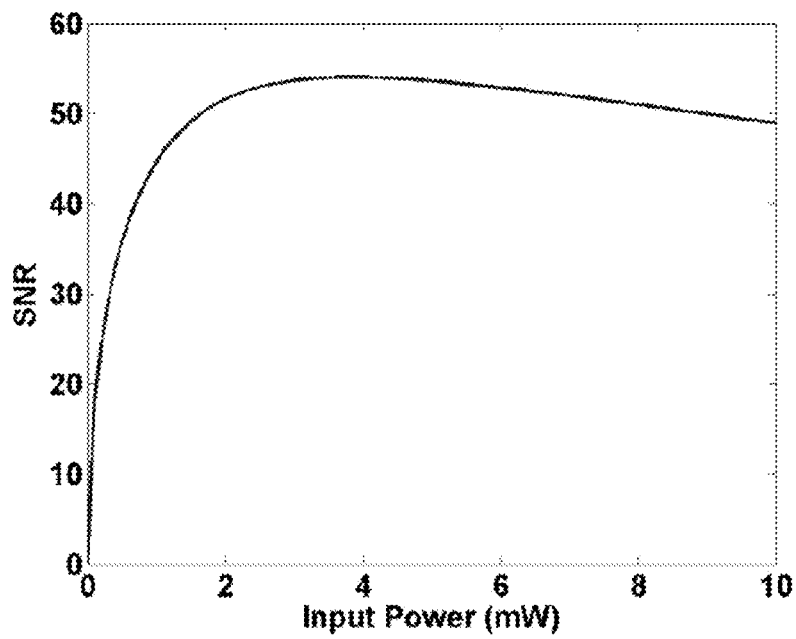
Figure 17C:
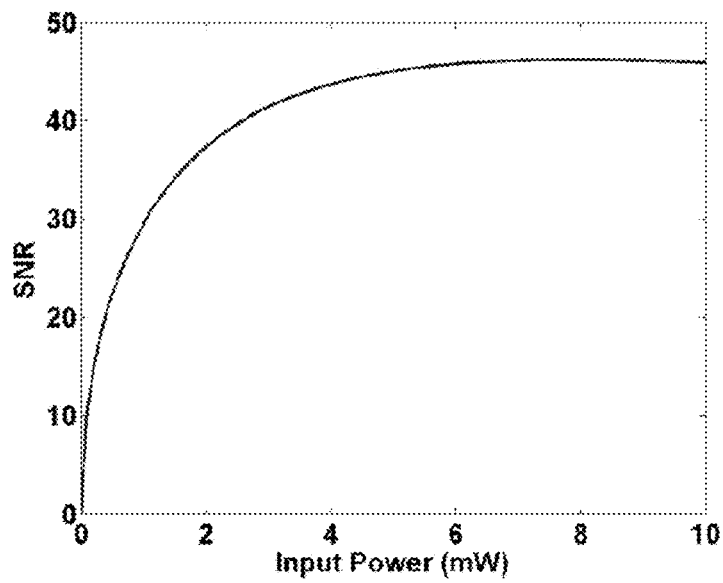
Figure 17D:
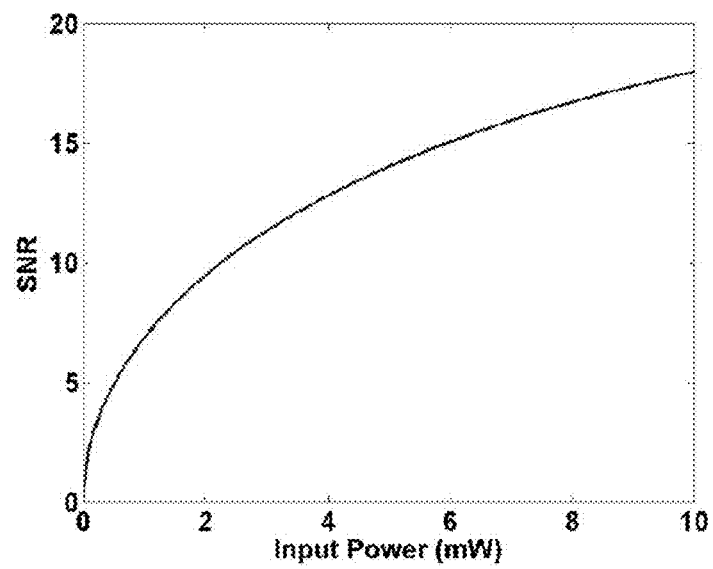
Figure 17E:
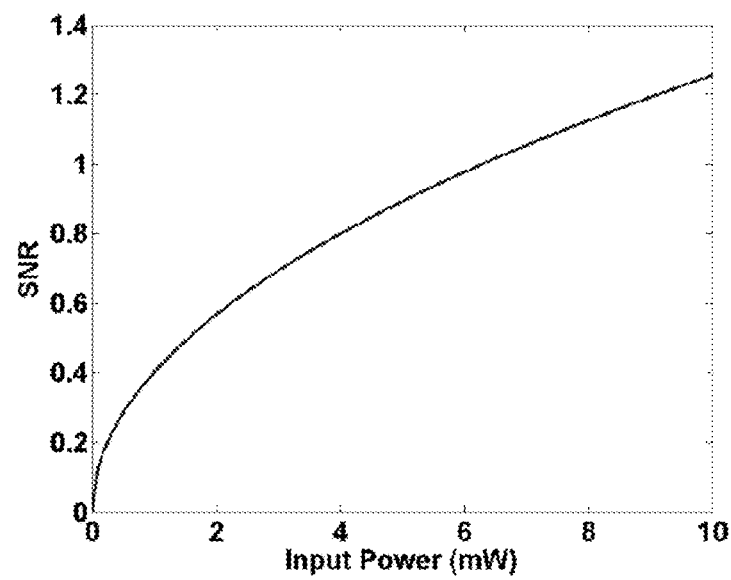
Figure 17F:
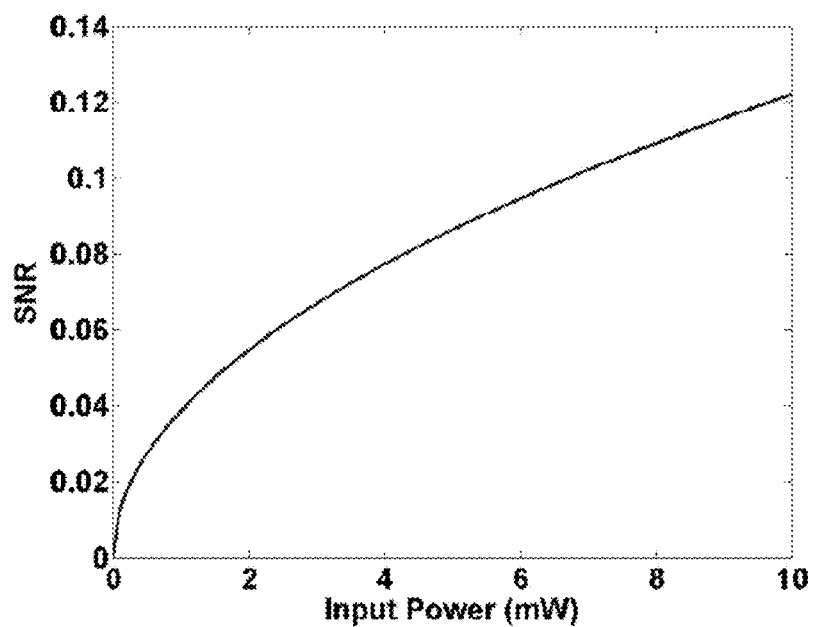
Figure 18A:
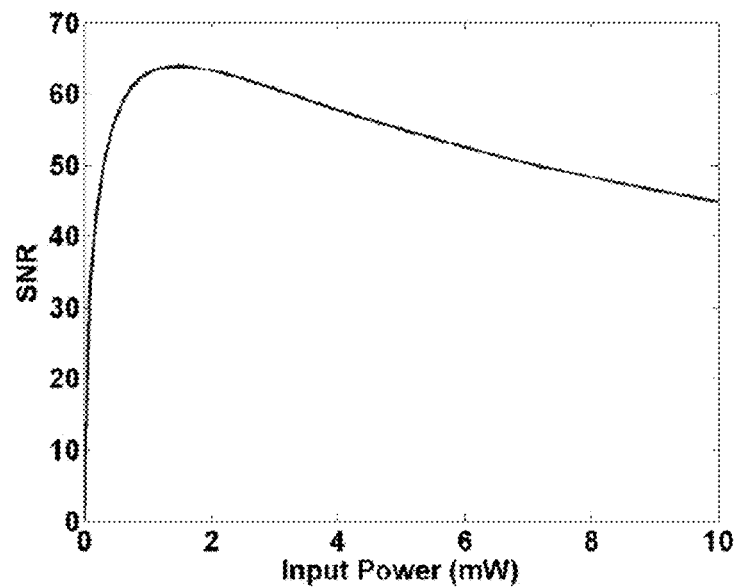
Figure 18B:
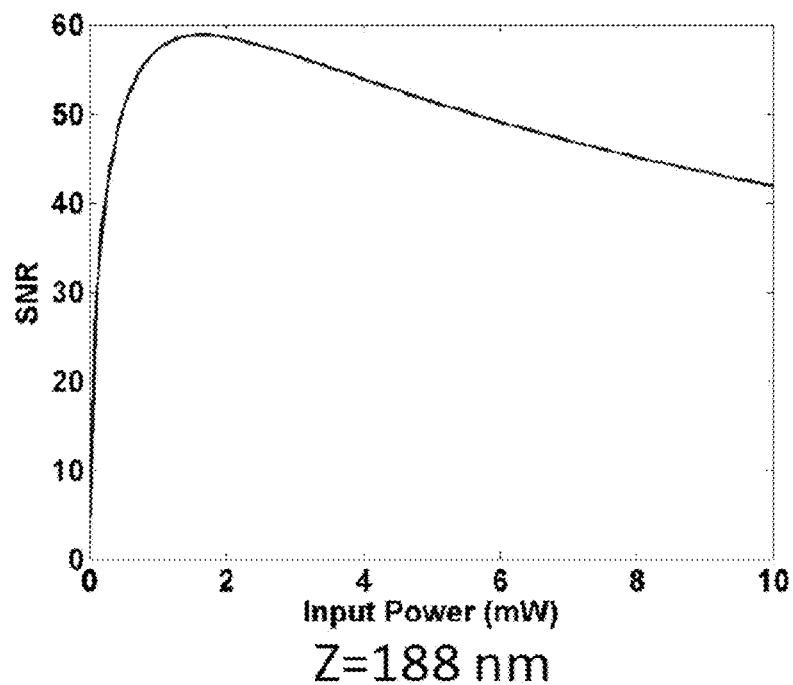
Figure 18C:
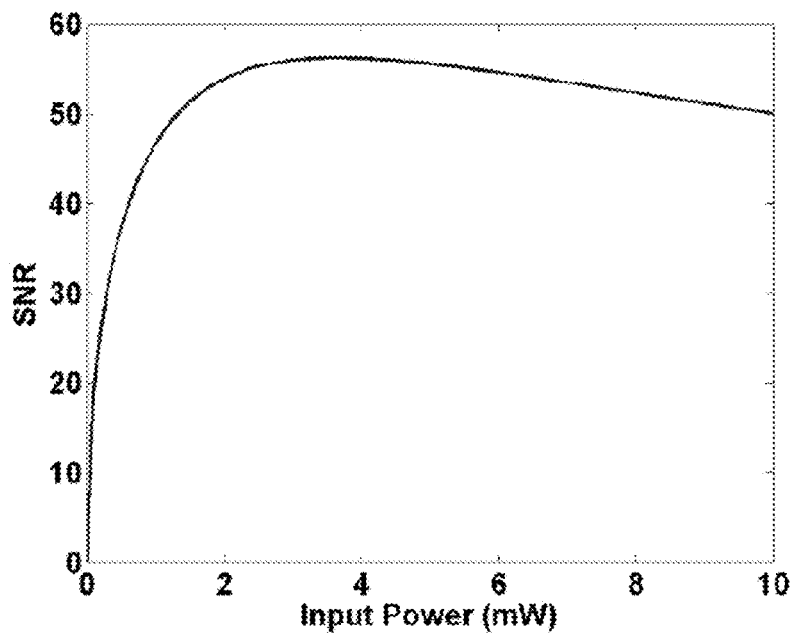
Figure 18D:
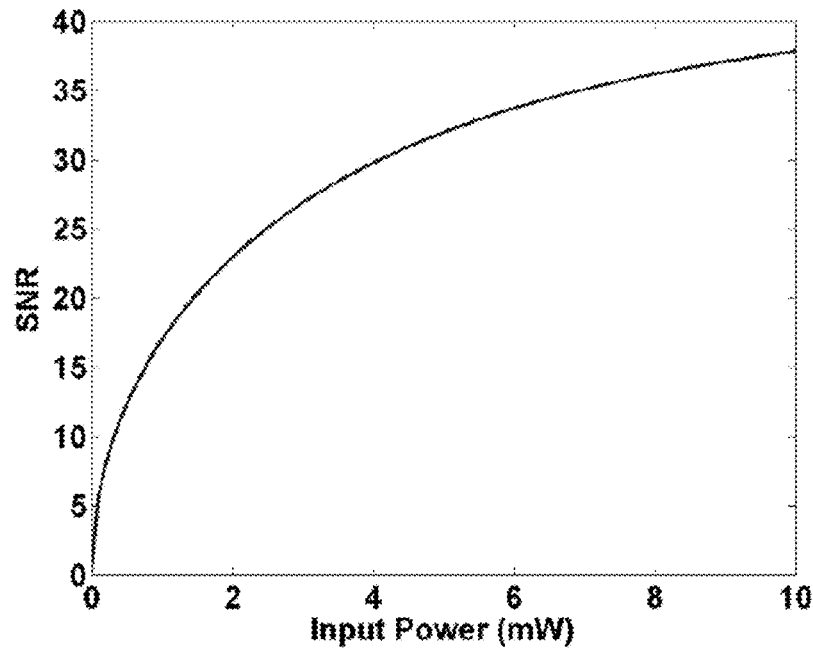
Figure 18E:
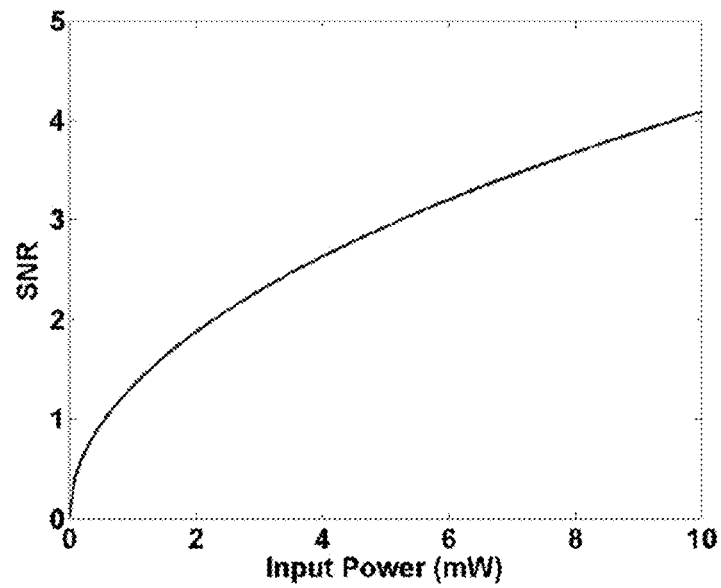
Figure 18F:
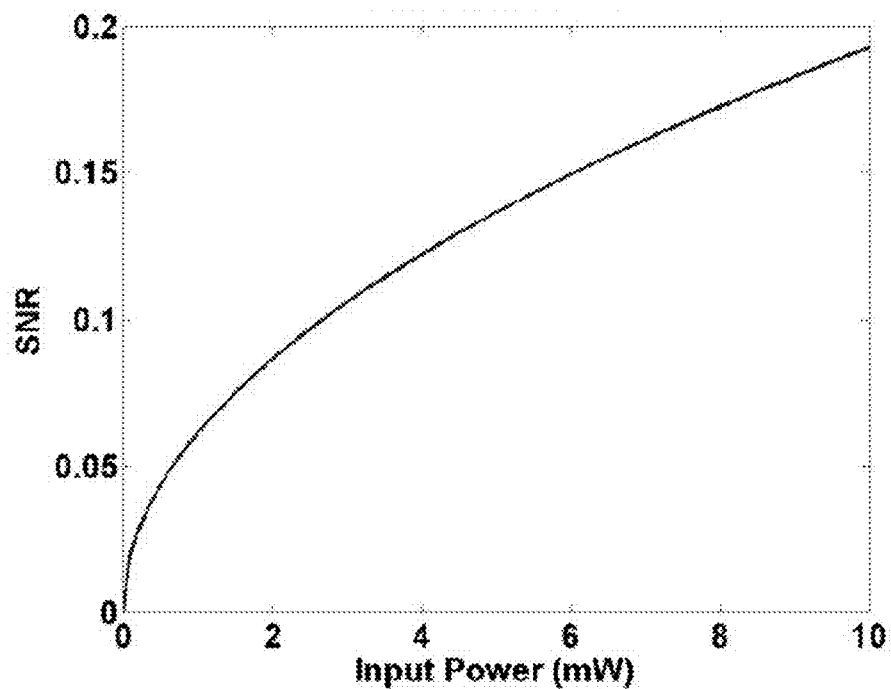

FIG. 16 illustrates the total efficiency of the waveguide structure as described above with a hole inside the waveguides and a hole not reaching through the waveguide but being positioned on the surface of the waveguide. The total efficiency thereby is given as function of the position of the hole relative to the center of the waveguide. It can be seen that the total efficiency drops when positioning the hole not in the center of the waveguide. Furthermore, it can be seen that providing a hole that reaches through the waveguide so the label can be positioned in the waveguide, results in the best efficiency. For this simulation, the label was positioned at the center height of the waveguide for a hole reaching till the bottom of the waveguide, and at a height of 10 nm above the surface of the waveguide, for a hole not reaching through the waveguide. The detection parameters used for the simulation were as follows: an integration time of 1 ms, a detector quantum efficiency of 1, a detector dark count of 100 count/s, an autoluminescence rate of 1 part per billion/100 nm. The propagation length was 200 m.

The signal to noise ratio (SNR) was calculated for both situations. The signal to noise ratio used is given by $$SNR = \frac{signal * time}{\sqrt{(Signal + Af + N_d) * time}}$$

whereby the signal is the number of photons form single molecules per second, Af are the autofluorescence photons per second and $N_d$ is the dark count rate per second.

FIG. 17*a* to FIG. 17*f* illustrates the signal to noise ratio versus the input power for different off-axis distances for the hole with respect to the excitation waveguide (while the hole stays centered with respect to the emission waveguide). The different off-axis distances are indicated in the different drawings. In FIG. 17*a* to FIG. 17*f* this is indicated for a hole that is not extending into the waveguide layer. FIG. 18*a* to FIG. 18*f* illustrates similar results for a waveguide structure whereby the hole is extending into the waveguide layer.

Figure 19:
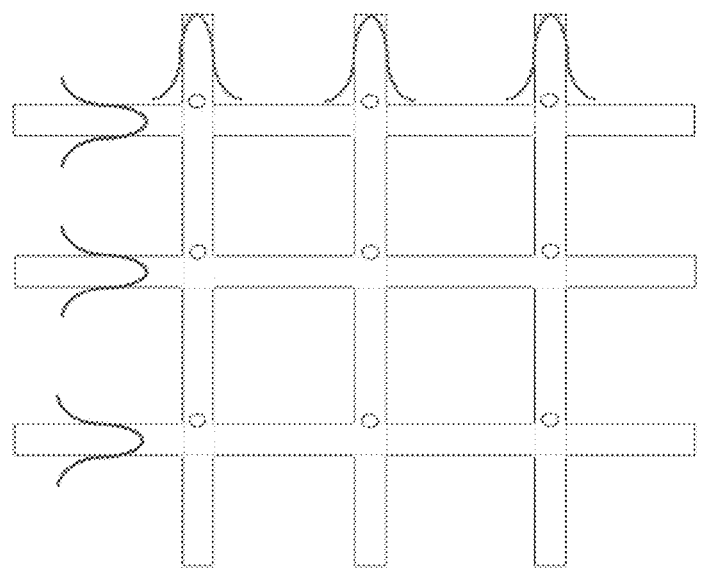
FIG. 19 illustrates an arrangement for multiple optical detections, according to an embodiment of the present invention.

In an embodiment of the present invention, a waveguide structure comprising a plurality of sensing sites is provided. A plurality of a set of excitation waveguides is orthogonal to a set of emission waveguides. Near each of the crossing points a sensing site and a particle radiation coupler is positioned. FIG. 19 is an exemplary embodiment of a waveguide structure comprising such a plurality of sensing sites.

Figure 8:
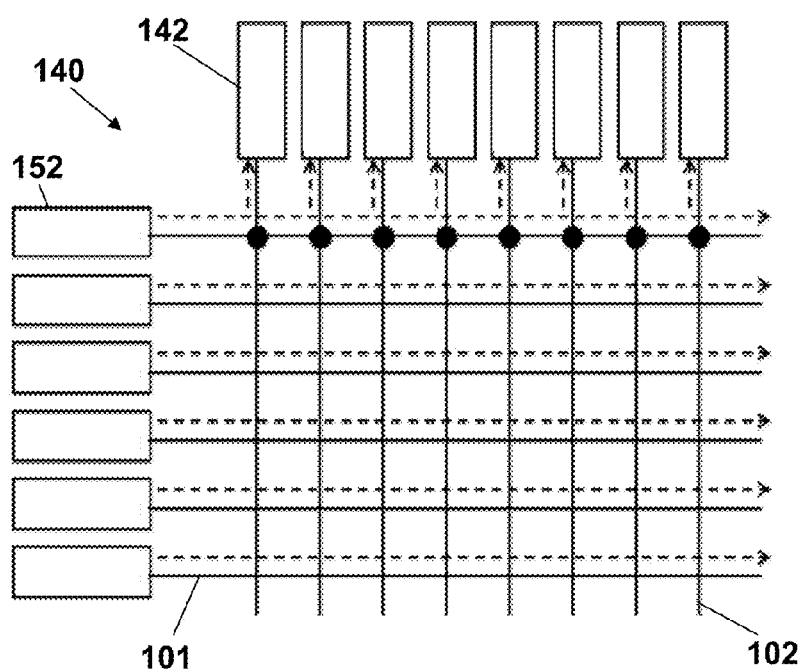
FIG. 8 shows an architecture for a system according to embodiments of the present invention.

In a second aspect, the present invention relates to a system comprising at least one waveguide structure according to the first aspect of the present invention. Referring to FIG. 8 and FIG. 9, the system 140 according to embodiments of the present invention further comprises at least one radiation source 152 for transmitting radiation through the excitation waveguide 101 of the at least one waveguide structure, and at least one detector 142 for detecting radiation transmitted by the emission waveguide 102 of the at least one waveguide structure 100.

A system according to embodiments may enable the on-chip integration of otherwise free-space optics to excite and collect single molecule fluorescence. Although parallelization of the read-out may still require the projection of the out-coupled fluorescence to a highly sensitive camera in the far-field in some embodiments of the invention, working with visible radiation on a silicon platform can also provide the unique opportunity to integrate the detectors directly with the emission waveguides. In such system with integrated detector, the photon losses related to the out-coupling are advantageously reduced, and therefor provide a high signal to noise ratio (SNR). Furthermore, good read-out speed and efficient parallelization on the chip can also be achieved in accordance with the present invention.

The at least one detector may for example comprise spectrometer for detection of the radiation emitted by the excited labels of bioparticles at the sensing site. In an embodiment of the present invention, the at least one detector may comprise a plurality of ring resonators, in which each ring resonator is tuned to a predetermined wavelength. A combination of resonators may also be used to couple out selective portions of the spectrum into separate detectors, as shown in FIG. 10.

In other embodiments of the invention, a multimode interference structure may be used to sense the radiation emitted by the labels. An emission waveguide may for example be locally enlarged to modify a single mode waveguide into a multimode waveguide. Radiation with a predetermined wavelength may then end up at a corresponding outfall due to interference effects.

An architecture of such system according to embodiments of the present invention may comprise a plurality of excitation waveguides arranged in rows for exciting the labels of different bioparticles located in corresponding columns and a plurality of emission waveguides arranged in columns for detecting the radiation emitted by the labels, e.g. as shown in FIG. 8. For example, the sensing sites may be functionalized differently in different columns, e.g. such that different bioparticles are captured and excited in corresponding columns.

In such architecture, each row may be excited by a corresponding radiation source. All labels of bioparticles, e.g. molecules with a fluorescent tag, which are excited by the radiation source of one row, can be read out in parallel by a plurality of detectors corresponding to the columns. The rows may for example receive a radiation pulse sequentially, e.g. such that in each time frame a next row of excited molecules can be read out. Each row may thus be read out before exciting the following row. Each row can thus be read, one after the other, until emissions in all rows are acquired. As an advantage, the detectors of each column can be reused for each row read out in a sequential manner. A time division multiplexing may be employed in which a single detector can be used to read out all excited molecules of one column. A corresponding controller for controlling the excitation and the read-out may be provided in the system.

The radiation that is emitted by the label of the bioparticle may reach the at least one detector unattenuated or with little attenuation. As according to some embodiments, the detectors may be shared by each row, the distance from the emitting labels to the detectors may increase. At each row/column intersection, e.g. at each waveguide crossing, additional nanostructures may be provided to reduce the radiation attenuation. Such additional nanostructures may ensure that the emitted radiation does not encounter sudden "shocks", e.g. discontinuities. In accordance with certain embodiments, an attenuation per crossing of 0.15 dB can be achieved, although this may be even further reduced by optimizing the design by simple experimentation.

The system may furthermore comprise a rejection filter suitable for rejecting radiation from the excitation waveguide 101. Thus, the excitation radiation may be prevented in reaching the detectors. For example, non-fluorescent radiation can be rejected or strongly attenuated by incorporating filter stacks on top of the detector, e.g. a detector integrated in the system. Such rejection filter may for example comprise an interference or absorption filter.

The system may also comprise butt couplers or grating couplers 151 for coupling radiation into the excitation waveguide 101 and/or out of the emission waveguide 102, for example as shown in FIG. 9. In an embodiment of the invention, a grating coupler structure may be used, e.g. a part of the waveguide may be enlarged, and the enlarged part may comprise a grating. The grating coupler may be used to excite the molecules of one row. To activate the grating coupler, a laser beam may be mechanically driven such that the laser beam scans the different grating coupler structures. This way, every waveguide may be sequentially addressed, e.g. using a sweeping radiation source such as a movable laser 152. Detection of the emitted radiation of the labels, e.g. of fluorescent tags of the molecules, can be done synchronous with the scanning. For example, when multiple wavelengths are being collected simultaneously via the emission waveguide, the collected wavelengths may be split prior to out-coupling using arrayed waveguide gratings (AWGs).

As the emission of single molecules can be very weak, the efficiency of the optical components in the analysis circuit may be very high. Therefore, certain embodiments may limit the amount of lossy structures, such as optical splitters. A grating coupler in a system according to some embodiments may provide a high efficiency of out-coupling, e.g. over 90% for a specific wavelength, for example by positioning a reflective mirror below the emission waveguide.

As the intensity of the excitation radiation may exceed the intensity of the emitted radiation with several orders of magnitude, it may not be completely filtered out by the resonator, e.g. the resonant cavity, and additional filtering may therefore be performed. The filter, e.g. an absorptive or interference filter, may be tuned to provide good rejection of the excitation wavelength.

The detector 142 may for example comprise a classical CMOS based detector or an avalanche photodiode (APD), e.g. which may advantageously allow for single photon resolution. In a system according to embodiments of the present invention, the at least one detector may be coupled to the emission waveguide 102 or integrated in the emission waveguide 102.

In such system according to embodiments of the present invention, the at least one radiation source may be integrated in the excitation waveguide 101.

Furthermore, the system may also comprise a microfluidic system for enabling a solution-based analysis. For example at least microfluidic channel may be provided to bring the bioparticle in a solution in contact with the sensing site of the waveguide structure 100, such that the bioparticle can be captured thereon. In some embodiments, the waveguide structure and/or the microfluidic system are adapted for inputting radiation into the excitation waveguide, e.g. with a laser coupled to the excitation waveguide, without having the radiation source interact with the solution.

In a third aspect, the present invention also relates to a method for analysing a fluorescent particle, e.g. a fluorescently labelled bioparticle. Referring to FIG. 11, the method 200 according to embodiments comprises coupling 201 radiation into an excitation waveguide 101 of an integrated waveguide structure 100, e.g. an integrated waveguide structure 100 according to embodiments of the first aspect of the present invention, and activating 202 a fluorescent particle positioned at a sensing site 103 of the integrated waveguide structure 100, in which this sensing site 103 is adapted for capturing the fluorescent particle and positioned such as to enable the activation of the label of the bioparticle by the radiation transmitted via the excitation waveguide 101.

The method also comprises coupling 203 radiation emitted by the fluorescent particle to an emission waveguide 102 of the integrated waveguide structure via a resonator 106, and detecting 204 the radiation emitted by the fluorescent particle and transmitted via the emission waveguide 102.

In a further aspect, the present invention also relates to the use of a system according to the second aspect of the present invention for sequencing DNA. The invention also relates to the use of a system according to the second aspect for detecting bioparticles.

For example, a system according to embodiments can be used for evaluating protein binding events in living intact cells. This can for example be used for studying protein kinetics on the membrane of individual cells. A system according to embodiments can advantageously enable the monitoring of single molecule binding kinetics on membranes of individual living cells using integrated microchips. This can, for example, be implemented in a multicolor FCS system with a plurality of different fluorescent dyes.

Furthermore, standard diagnostic assays are becoming increasingly important, especially considering the growing population of elderly and immune compromised people. Therefore, the integration of a multiplex, wash-free cytokine assay may provide advantageous means for diagnosis. Although a plethora of assays is currently available, most immune related reactions in the body have a cytokine component. Therefore, the ability to sense multiple cytokines directly in cell cultures as well as in clinical samples can provide a wealth of information for clinical diagnosis. The ability to sense binding in a high background allows to develop wash-free assays as well as to sense responses in real-time and measure binding kinetics. Together with the high miniaturization of integration potential, the present invention can provide fast, wash-free portable sensing devices. Such systems allow for near patient diagnostics at the emergency department or the monitoring of severe infections and inflammatory diseases of critical care patients, including sepsis which remains a major cause of death. The monitoring of pro-inflammatory cytokines (TNF-a, IFN-g, IL-1, IL-6) as well as anti-inflammatory cytokines (IL-4, Il-10 and IL-18) may be important diagnostic markers as sepsis or a systemic inflammatory response are characterized by an inability to regulate the inflammatory response. The actual cause of this perturbation is still unknown, but several decades of research did not result in a dramatic reduction of mortality rates and may vary from 30 to 70% for critically ill patients in intensive care units.

For example, a singleplex TNFalpha assay may be provided in accordance with embodiments of the present invention. $SiO_2$ coated waveguides can be functionalized with an amino-silane to covalently couple antibodies in a specific manner. After coupling, different concentrations of TNFa and fluorescent labelled secondary antibodies may be added. The binding can be measured in real-time and characterized towards on- and off rates as well as towards sensitivity, first in buffer, later in serum samples. Furthermore, similar assays for other cytokines may be added. For detection of several cytokines in a multiplex assay, secondary antibodies may be labelled with fluorophores emitting radiation at different wavelengths. Alternatively, the different primary antibodies may be spotted at different nano-apertures. Furthermore, the $SiO_2$ area next to the nano-apertures may be passivated, such that potential background contributions may be avoided, and the sensitivity can be increased.

For example, a system according to embodiments of the present invention may comprise a multiplexed wash-free sensing assay for the direct detection of cytokines. Cytokines are small cell signalling proteins involved in the immune-response of humans towards many disease states, e.g. infections, cancer and Alzheimer's disease. The system according to embodiments is particularly suitable for the fast detection of low cytokine concentrations at the early onset of sepsis, an acute inflammatory immune reaction with a high mortality rate even in the western world. Early detection of small concentrations of these proteins allows detecting of the onset of sepsis, thereby improving the prognosis. State of the art biosensor methodologies may struggle to get detection limits down to the clinically relevant sensitivity limits, e.g. lower than a few pg/ml for relevant cytokines such as TNF-a, IL6 and IL10. For example, the technique of reference in cytokine detection is ELISA, an enzymatically catalysed fluorescent immunoassay. Analysis is typically performed in robotized systems in centralized labs with many complicated consecutive assay steps. The ELISA protocol is powerful, sensitive and specific, but not easy to bring to the point-of-care. As a result, patient samples may spend a lot of time in transportation and may be analysed too late for saving lives. The by the present invention disclosed technology can provide a wash-free assay where single molecules can be detected in real time. Multiplexing can be obtained simply by placing multiple sensing spots in parallel. The large number of sensing sites together with an advantageous nanofluidic design can also help to overcome the limitation imposed by diffusion kinetics of very lowly concentrated samples. Besides the obvious benefits of a multiplex, real-time and wash-free assay, the present invention provides a highly scalable and integratable potential for realizing portable systems. The use of such integrated nanophotonic circuits can result in highly sensitive integrated fluorescence sensors, implemented at the nanoscale and without the need for expensive and bulky free space optics. This can find application in, for example, rapid screening of enzyme kinetics on cell surfaces, cheap DNA sequencing and sensitive wash-free biosensing assays.

In one aspect, the present invention also relates to a system for optically detecting particles, such as for example biomolecular particles, translocating through a nanopore. It thereby is an advantage of embodiments of the present invention that the particles, e.g. biomolecular particles do not need to be labelled. The system's operation is based on a waveguide structure or a characterisation system according to the present invention combined with the following principle: A chemical cell with two reservoirs separated by a membrane is used, the membrane comprising a nanopore through which the reservoirs are connected. At one side there are ion-sensitive fluorescent dyes (i.e. dyes for which the amplitude of the fluorescence depends on the local concentration of certain ions (elements) such as Calcium). The other reservoir is loaded with such ions, e.g. calcium ions. When an electric field is generated and thus a potential is applied, a current can flow through the pore. When the right polarity is applied, the ions flow through the pore, locally increasing the ion concentration and increasing/ decreasing the fluorescence of the ion-sensitive fluorescent dyes. When the current drops, due to e.g. a DNA strand that translocates through the pore and that blocks the ionic current, the local ion concentration drops and the fluorescence level drops as well. According to embodiments of the present invention, the ion-sensitive fluorescent dyes are activated and fluorescence is detected using a waveguide structure as described in the first aspect or a characterisation system as described in the second aspect. In some embodiments, the membrane may be or comprise the waveguide structure, or in other words, the waveguide structure may behave as a membrane. In such embodiments, the waveguide structure thus comprises a nanopore and the sensing site is at or in the nanopore. In another embodiment, the membrane and the waveguide structure are two distinct elements. The membrane and the waveguide structure may be positioned close to each other. The nanopore in the membrane and a cavity in the waveguide structure may be aligned with respect to each other and the sensing site may be positioned in the cavity. In the present application the system thus is adapted for continuously or quasicontinuously monitoring the fluorescence and detecting whether or not a drop in fluorescence occurs. Such a drop in fluorescence then is representative for the passing of a particle through the nanopore being not an ion that influences the fluorescence.

Figure 20:
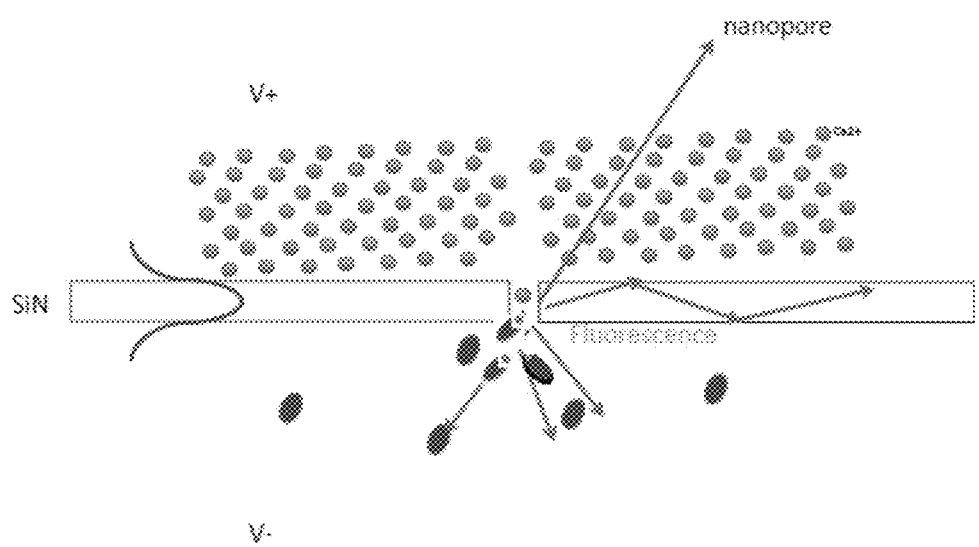
FIG. 20 and FIG. 21 illustrate systems for optically detecting transmission through a nanopore, according to embodiments of the present invention.
Figure 21:
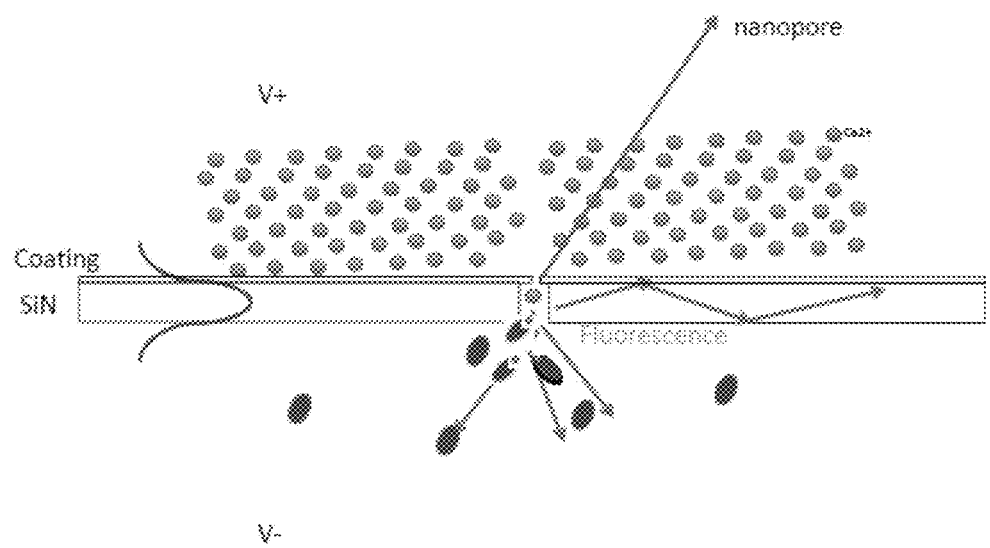

FIGS. 20 and 21 illustrate two different embodiments of systems allowing optical detection of translocation of a particle through a nanopore. FIG. 20 illustrates an example wherein the waveguide structure provides a nanopore and thus acts as a membrane, whereas FIG. 21 illustrates an example wherein a combination of a membrane with a nanopore and a waveguide structure is used for optical detection of translocation of a particle through a nanopore.

Figure 22:
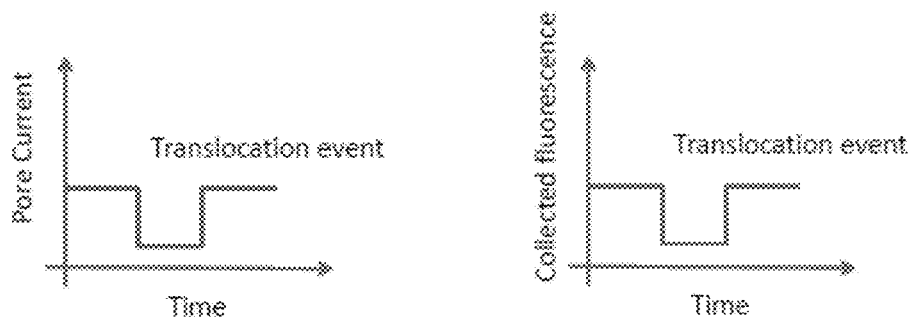
FIG. 22 shows a schematic representation of the pore current and the collected fluorescence identifying a translocation event, illustrating features and advantages of embodiments of the present invention.

FIG. 22 illustrates a schematic example of the detection of a translation event as can be detected in the pore current as function of time as well as in the detected fluorescence as function of time.

In a particular aspect, the present invention also relates to a method for optically detecting the translocation of particles in a label free manner. In one embodiment, the method comprises the following steps:

Providing a chemical cell comprising two reservoirs separated by a membrane but in contact with each other through a nanopore, one reservoir comprising an ion-sensitive fluorescent dye, e.g. a calcium sensitive fluorescent dye, and the other reservoir comprising such ions that influence the fluorescent dye.

Applying an electric field (thus inducing a potential difference) over the membrane, thus generating an ion flow, e.g. calcium ion flow, through the nanopore of the membrane thus creating an ion flow in the ion-sensitive fluorescent dyes and thus providing an influence of the fluorescence character of the dyes, Inducing and collecting fluorescence using a method as described in the third aspect, whereby the fluorescence is captured from the ion-sensitive fluorescent dyes during the ion flow, deriving, based on said optical detecting, a point in time that the ion flow is reduced representative for a particle translocating the pore and blocking the ion flow.

Further features and aspects may be present, expressing the functionality of the components of the systems. Features and advantages may be as obtained by the system and method described in the first, second and third aspect.

The invention claimed is:

1. An integrated waveguide structure, comprising:
a substrate;
a waveguide layer arranged on top of the substrate, the waveguide layer comprising:
one or more excitation waveguides configured to transmit excitation radiation to activate a fluorescent particle;
one or more emission waveguides, distinct from the one or more excitation waveguides, configured to transmit radiation emitted by the fluorescent particle; and
a particle radiation coupler, wherein the particle radiation coupler comprises a resonator element arranged to couple radiation emitted by the fluorescent particle into at least one of the emission waveguides in response to the activation by the excitation radiation transmitted via the one or more excitation waveguides; and
one or more sensing sites configured with respect to the one or more excitation waveguides and the one or more emission waveguides such that a fluorescent particle at one of the sensing sites is activated by the excitation radiation transmitted via the one or more excitation waveguides and radiation emitted by the fluorescent particle is coupled into at least one of the emission waveguides by the particle radiation coupler,
wherein the resonator element is positioned between at least one of the emission waveguides and at least one of the excitation waveguides, and
wherein at least one of the sensing sites is positioned between at least one of the excitation waveguides and the resonator element.

2. The integrated waveguide structure according to claim 1,
wherein the integrated waveguide structure further comprises a sensing layer arranged on top of the waveguide layer, wherein the one or more sensing sites are on top of the sensing layer, and
wherein the one or more sensing sites are disposed in a cavity in the sensing layer or in a cavity extending through the sensing layer and into the waveguide layer.

3. The integrated waveguide structure according to claim 1, wherein the one or more sensing sites are positioned with respect to the one or more excitation waveguides so as to enable the activation of the fluorescent particle by an evanescent field of the excitation radiation propagating through the one or more excitation waveguides.

4. The integrated waveguide structure according to claim 1,
wherein the particle radiation coupler is a disk resonator, a ring resonator, a linear resonator, or a photonic crystal resonator, and
wherein the particle radiation coupler is tuned to couple radiation having a wavelength corresponding to a wavelength of a fluorescence emission of the fluorescent particle.

5. The integrated waveguide structure according to claim 1, wherein the particle radiation coupler is positioned in at least one of the emission waveguides or in a near field region thereof.

6. The integrated waveguide structure according claim 1, wherein at least one of the sensing sites is located above the one or more emission waveguides.

7. The integrated waveguide structure according to claim 1,
wherein a direction of at least one of the excitation waveguides is substantially orthogonal to a direction of at least one of the emissions waveguides, thereby forming crossing waveguides.

8. The integrated waveguide structure according to claim 1,
wherein at least one of the excitation waveguides is connected to at least one of the emission waveguides.

9. The integrated waveguide structure according to claim 7,
wherein the at least one sensing site is positioned above or in the at least one emission waveguide, away from a center of a point of crossing of the crossing waveguides, and
wherein the at least one sensing site is positioned off-center with respect to the at least one emission waveguide.

10. The integrated waveguide structure according to claim 1,
wherein at least one of the excitation waveguides comprises a mode expander, and
wherein the mode expander is positioned at or near at least one of the sensing sites so that excitation radiation at the position of the mode expander can excite the fluorescent particle.

11. The integrated waveguide structure according to claim 1,
wherein the one or more excitation waveguides comprise a plurality of substantially parallel excitation waveguides,
wherein the one or more emission waveguides comprise a plurality of substantially parallel emission waveguides that cross the plurality of substantially parallel excitation waveguides, and
wherein the one or more sensing sites comprise a plurality of sensing sites each located at a crossing of an excitation waveguide and an emission waveguide.

12. The integrated waveguide structure according to claim 1, wherein at least one of the sensing sites has a surface chemistry adapted for capturing the fluorescent particle or at least one of the sensing sites comprises a cavity that is smaller than a wavelength of the excitation radiation.

13. A characterization system for characterizing at least one fluorescent particle, the characterization system comprising:
an integrated waveguide structure, the integrated waveguide structure comprising:
a substrate;
a waveguide layer arranged on top of the substrate, the waveguide layer comprising:
one or more excitation waveguides configured to transmit excitation radiation to activate a fluorescent particle;
one or more emission waveguides, distinct from the one or more excitation waveguides, configured to transmit radiation emitted by the fluorescent particle; and
a particle radiation coupler, wherein the particle radiation coupler comprises a resonator element arranged to couple radiation emitted by the fluorescent particle into at least one of the emission waveguides in response to the activation by the excitation radiation transmitted via the one or more excitation waveguides; and
one or more sensing sites configured with respect to the one or more excitation waveguides and the one or more emission waveguides such that a fluorescent particle at one of the sensing sites is activated by the excitation radiation transmitted via the one or more excitation waveguides and radiation emitted by the fluorescent particle is coupled into at least one of the emission waveguides by the particle radiation coupler,
wherein the resonator element is positioned between at least one of the emission waveguides and at least one of the excitation waveguides, and
wherein at least one of the sensing sites is positioned between at least one of the excitation waveguides and the resonator element;
one or more excitation radiation sources configured to transmit the excitation radiation through at least one of the excitation waveguides; and
one or more detectors configured to detect radiation transmitted by at least one of the emission waveguides.

14. The characterization system according to claim 13, wherein at least one of the detectors is an integrated detector integrated in the at least one of the emission waveguides, or at least one of the excitation radiation sources is an integrated radiation source integrated in the at least one of the excitation waveguides, or at least one of the detectors comprises a rejection filter suitable for rejecting the excitation radiation transmitted by at least one of the excitation waveguides.

15. The characterization system according to claim 13,
wherein the one or more excitation waveguides comprise a plurality of substantially parallel excitation waveguides,
wherein the one or more emission waveguides comprise a plurality of substantially parallel emission waveguides that cross the plurality of substantially parallel excitation waveguides,
wherein the one or more sensing sites comprise a plurality of sensing sites each located at a crossing of an excitation waveguide and an emission waveguide,
wherein the characterization system further comprises excitation facilities for each of the substantially parallel emission waveguides and detection facilities for each of the emission waveguides, and
wherein the characterization system further comprises a controller programmed to sequentially activate different sets of fluorescence particles by sequentially transmitting excitation radiation in the excitation waveguides.

16. The characterization system according claim 13,
wherein the characterization system further comprises a chemical cell, the chemical cell comprising two reservoirs separated by a membrane, the two reservoirs being connected through a nanopore in the membrane,
wherein one of the reservoirs comprises ion-sensitive fluorescent dyes and the other reservoir comprises ions for which the fluorescent dyes are sensitive, and
wherein the chemical cell further comprises an electric field generator configured to induce an electric field over the membrane for inducing an ion flow towards the reservoir with the ion-sensitive fluorescent dyes.

17. The characterization system according to claim 16, wherein at least one of the sensing sites is arranged to sense the ion-sensitive fluorescent dyes influenced by ion flow.

18. The characterization system according to claim 16, wherein at least one of the detectors is adapted to detect a variation in fluorescence of the ion-sensitive fluorescent dyes or the membrane is formed by the integrated waveguide structure.

19. A method for characterizing one or more fluorescent particles, the method comprising:
   transmitting excitation radiation into one or more excitation waveguides of an integrated waveguide structure;
   activating at least one of the fluorescent particles positioned at a sensing site of the integrated waveguide structure, wherein the sensing site is configured such that a fluorescent particle at the sensing site is activated by the excitation radiation transmitted via at least one of the excitation waveguides and radiation emitted by the fluorescent particle is coupled into an emission waveguide of the integrated waveguide structure;
   coupling, by a particle radiation coupler, radiation emitted by the fluorescent particle to the emission waveguide of the integrated waveguide structure, wherein the emission waveguide is distinct from the excitation waveguides,
   wherein the particle radiation coupler is a resonator element positioned between at least one of the excitation waveguides and the emission waveguide, and
   wherein the sensing site is positioned between at least one of the excitation waveguides and the resonator element; and
   detecting radiation emitted by the fluorescent particle and transmitted via the emission waveguide.

20. The method according to claim 19, wherein the fluorescent particles are ion-sensitive fluorescent dyes, and wherein the method further comprises:
   generating an ion flow through a nanopore of a membrane towards ion-sensitive fluorescent dyes positioned at the sensing site; and
   deriving, based on the detected radiation, a point in time that the ion flow is reduced, which is representative of a particle translocating the nanopore and blocking the ion flow.

* * * * *